(12) United States Patent
Aoki et al.

(10) Patent No.: US 9,526,523 B2
(45) Date of Patent: Dec. 27, 2016

(54) EXTERNAL FIXATION DEVICE AND FIXATION DEVICE SET

(71) Applicants: HITACHI METALS, LTD., Tokyo (JP); HIROSHIMA UNIVERSITY, Higashihiroshima-shi, Hiroshima (JP)

(72) Inventors: Masaaki Aoki, Takasaki (JP); Mitsuo Ochi, Hiroshima (JP)

(73) Assignees: HITACHI METALS, LTD., Tokyo (JP); HIROSHIMA UNIVERSITY, Higashihiroshima-shi (JP)

( * ) Notice: Subject to any disclaimer, the term of this patent is extended or adjusted under 35 U.S.C. 154(b) by 39 days.

(21) Appl. No.: 14/407,750

(22) PCT Filed: Jun. 11, 2013

(86) PCT No.: PCT/JP2013/066094
§ 371 (c)(1),
(2) Date: Dec. 12, 2014

(87) PCT Pub. No.: WO2013/187413
PCT Pub. Date: Dec. 19, 2013

(65) Prior Publication Data
US 2015/0127001 A1 May 7, 2015

(30) Foreign Application Priority Data
Jun. 15, 2012 (JP) ................. 2012-135636

(51) Int. Cl.
*A61B 17/00* (2006.01)
*A61B 17/66* (2006.01)
(Continued)

(52) U.S. Cl.
CPC ........... *A61B 17/66* (2013.01); *A61B 17/6425* (2013.01); *A61B 2017/00876* (2013.01); *A61B 2017/567* (2013.01)

(58) Field of Classification Search
CPC ....................... A61B 17/60–17/666
See application file for complete search history.

(56) References Cited

U.S. PATENT DOCUMENTS

| | | | | |
|---|---|---|---|---|
| 4,312,336 A | * | 1/1982 | Danieletto | A61B 17/6458 403/137 |
| 4,584,995 A | * | 4/1986 | Koeneman | A61B 17/66 606/54 |

(Continued)

FOREIGN PATENT DOCUMENTS

| | | |
|---|---|---|
| JP | 2002-345837 A1 | 12/2002 |
| JP | 2005-245470 A1 | 9/2005 |

(Continued)

OTHER PUBLICATIONS

International Search Report for International Application No. PCT/JP2013/066094 dated Aug. 6, 2013.
EP13804952: Extended European Search Report dated Feb. 2, 2016.

*Primary Examiner* — Jan Christopher Merene
*Assistant Examiner* — Steven Cotroneo
(74) *Attorney, Agent, or Firm* — Kratz, Quintos & Hanson, LLP

(57) ABSTRACT

A fixation device set S includes an external fixation device which is attached on one end-side of first and second pins; and a pin fixture which is attached on the other end-side. The external fixation device includes a first and a second permanent magnets disposed with their same poles opposed to each other; a first holding portion provided in the first permanent magnet; a second holding portion provided in the second permanent magnet; first limiter portions sandwiching the first and the second permanent magnets from a second direction; and second limiter portions connecting the first limiter portions to each other. The first pins are inserted through through-holes in the first holding portion, whereas (Continued)

the second holding portion is attached to the second pin via a ball joint.

9 Claims, 30 Drawing Sheets

(51) Int. Cl.
*A61B 17/64* (2006.01)
*A61B 17/56* (2006.01)

(56) References Cited

U.S. PATENT DOCUMENTS

| | | | |
|---|---|---|---|
| 4,604,997 A * | 8/1986 | De Bastiani | A61B 17/6425 |
| | | | 602/16 |
| 6,203,548 B1 | 3/2001 | Helland | |
| 2002/0151978 A1 * | 10/2002 | Zacouto | A61B 17/68 |
| | | | 623/17.12 |
| 2003/0187510 A1 * | 10/2003 | Hyde | A61N 2/06 |
| | | | 623/18.12 |
| 2009/0318976 A1 | 12/2009 | Gabriel et al. | |
| 2012/0053644 A1 | 3/2012 | Landry et al. | |

FOREIGN PATENT DOCUMENTS

| | | |
|---|---|---|
| JP | 2008-245730 A1 | 10/2008 |
| JP | 2012-157377 A1 | 8/2012 |
| WO | WO 99/02097 A1 | 1/1999 |
| WO | 2013/006291 A2 | 1/2013 |

* cited by examiner

F I G. 4
(a)
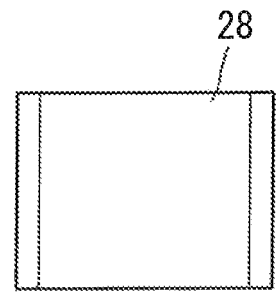
(b)
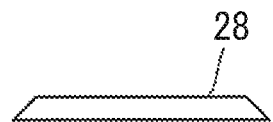

FIG. 5
(a)
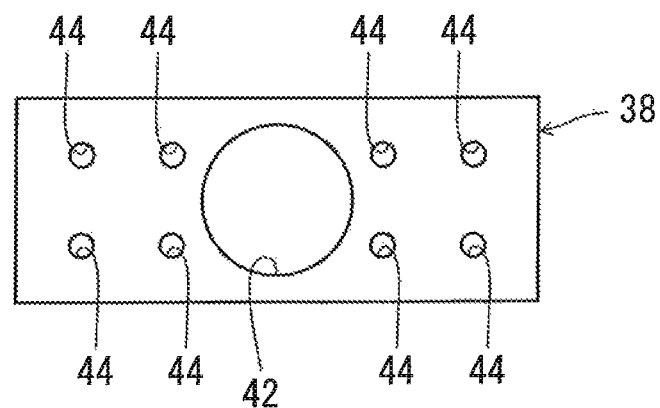
(b)
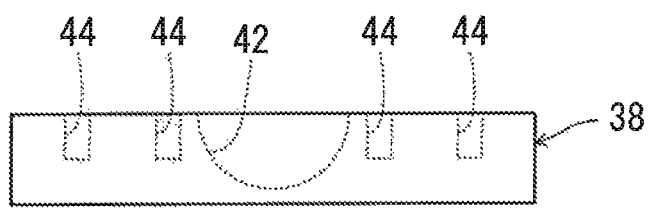

FIG. 6
(a)
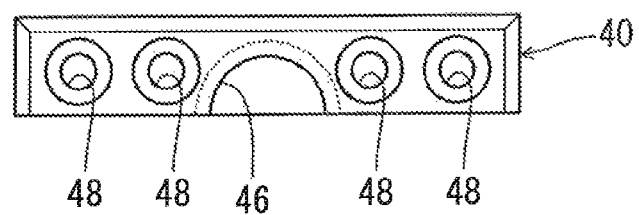
(b)
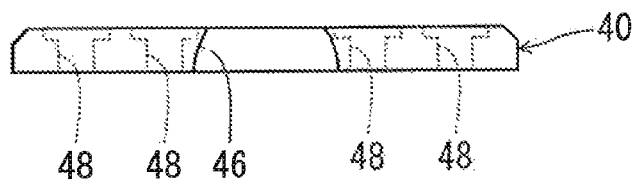
(c)
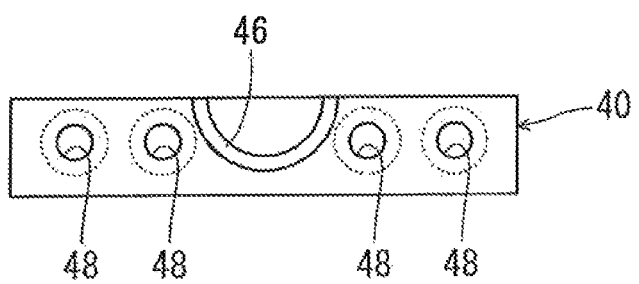

FIG. 9
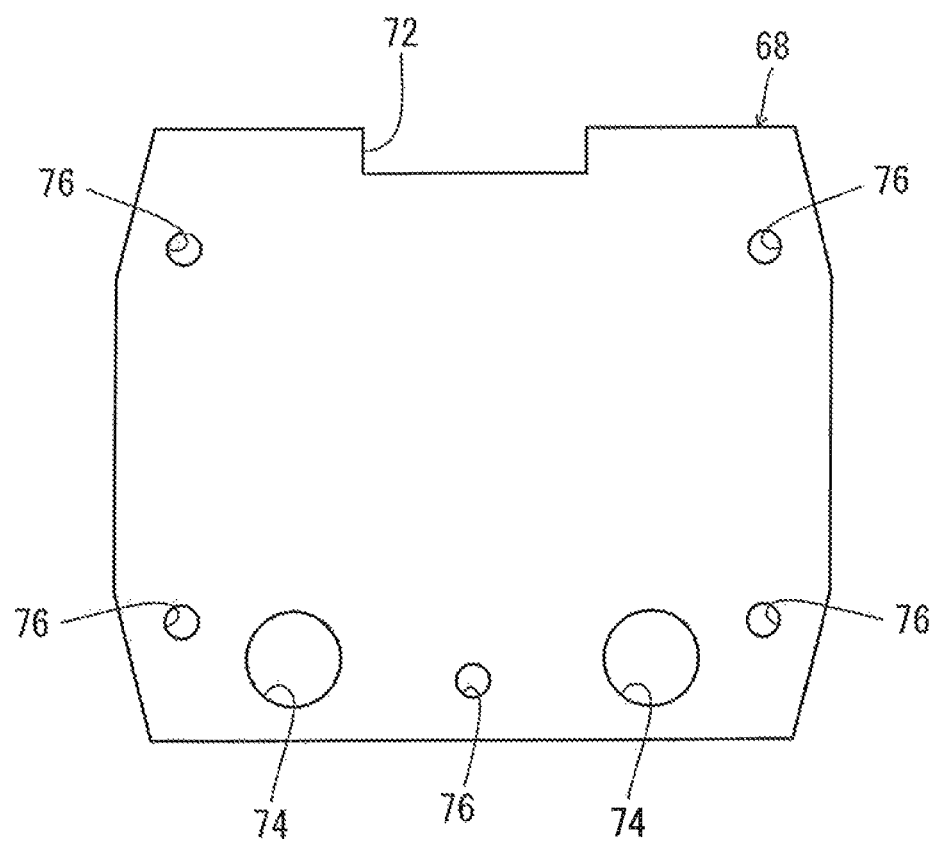

FIG. 10
(a)
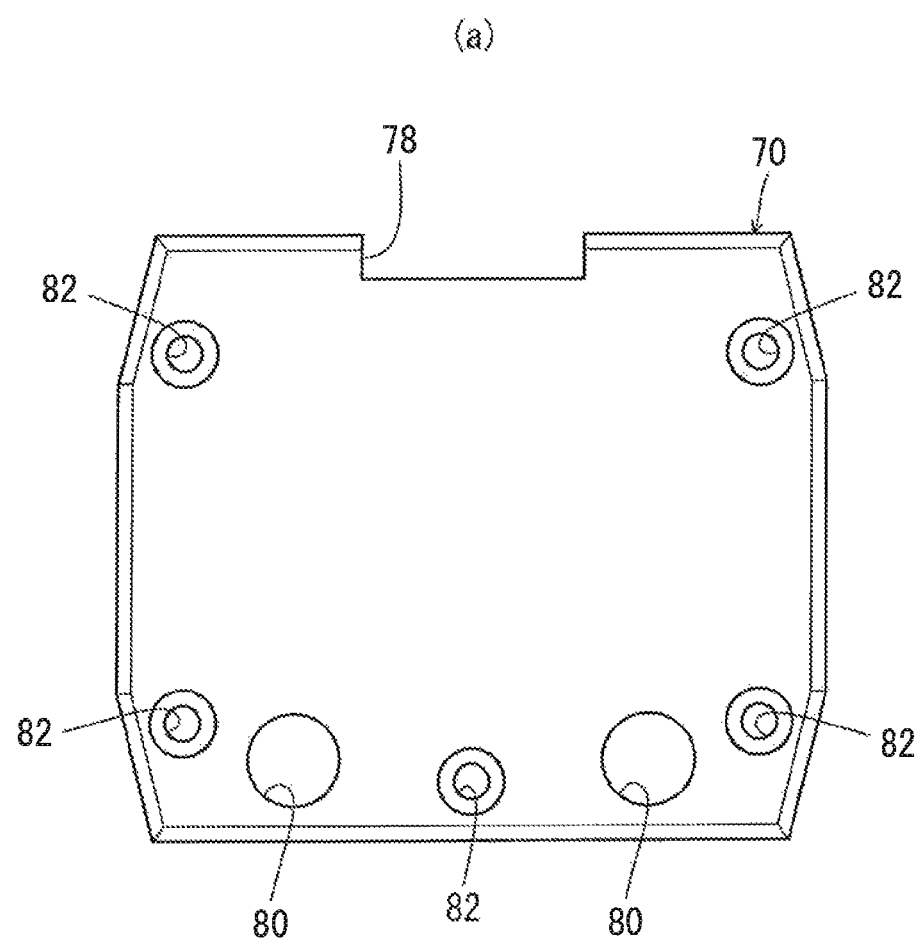
(b)
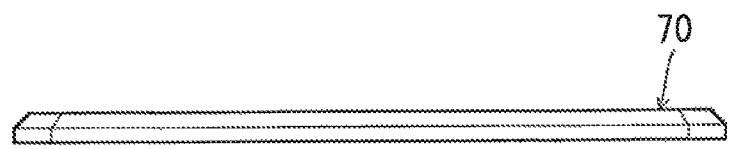

(a)  (b)

EXTERNAL FIXATION DEVICE AND FIXATION DEVICE SET

TECHNICAL FIELD

The present invention relates to external fixation devices and fixation device sets, and more specifically to an external fixation device and a fixation device set used in treating articular cartilage damage.

BACKGROUND ART

Extensive articular cartilage damage is treated typically by making a small hole in the damaged area using a drill, or an awl to stimulate bleeding from bone marrow thereby introducing bone marrow mesenchymal cells into the joint. Applying a load, however, to the damaged part soon after the operation poses a risk of damaging still immature tissues.

Patent Literature 1 discloses an example of an external fixation device which can be utilized in such a treatment of an articular cartilage damage. The external fixation device includes ball joints and a gear box, sandwiches the joint and mechanically fixes two sides of the joint in order to protect the damaged part, so that joint bone parts are separated from each other and the damaged part will have a reduced load. Then, with the external fixation device attached, the patient moves the joint.

CITATION LIST

Patent Literature

Patent Literature 1: JP-A 2002-345837
Patent Literature 2: JP-A 2005-245470

SUMMARY OF INVENTION

Technical Problem

However, the external, fixation device disclosed in Patent Literature 1 includes a large number of parts and has a complicated structure.

Patent Literature 2 discloses an external fixation device which includes a magnet. However, in this external fixation device, a pair of magnetic bodies, one of which fixed to a first bone portion and the other fixed to a second bone portion, contract to each other when the device is used, and cannot be utilized in treating an articular cartilage damage where the first bone portion and the second bone portion in a joint must be separated from each other.

Therefore, a primary object of the present invention is to provide an external fixation device which includes a decreased number of parts and has a simple structure yet is capable of separating a first bone portion and a second bone portion from each other in a joint thereby making possible to effectively treating the articular cartilage damage; and to provide a fixation device set.

Solution to Problem

According to an aspect of the present invention, there is provided an external fixation device for keeping a first bone portion and a second bone portion separated from each other in a joint, by attaching to a first pin which penetrates the first bone portion and to a second pin which penetrates the second bone portion. The device includes a first permanent magnet and a second permanent magnet which are opposed to each other, with their same poles facing each other; a first holding portion which is disposed on a surface of the first permanent magnet, on a side facing away from a surface opposing to the second permanent magnet, and is attached to the first pin; a second holding portion which is disposed on a surface of the second permanent magnet, on a side facing away from a surface opposing to the first permanent magnet, and is attached to the second pin; and a pair of first limiter portions which allow movement of the first permanent magnet and the second permanent magnet in a first direction defined as a direction of their repulsion force by sandwiching the first permanent magnet and the second permanent magnet from a second direction defined as a direction perpendicular to the first direction, and limit movement thereof in the second direction.

In the present invention, the first permanent magnet and the second permanent magnet are disposed with their same poles opposed to each other, and a pair of first limiter portions sandwich the first permanent magnet and the second permanent magnet. Therefore, the first permanent magnet and the second permanent magnet repulse against each other, moving away from each other in the direction of the repulsion force, i.e., in the first direction. As a result, the first pin which is connected to the first permanent magnet via the first holding portion, and the second pin which is connected to the second permanent magnet via the second holding portion, move away from each other. This makes it possible to move a joint, with its first bone portion and second bone portion kept apart from each other, i.e., with the cartilage part of the cleft between articulations kept open. By utilizing the repulsion force between the first permanent magnet and the second permanent magnet as described above, it becomes possible to reduce the number of parts and simplify the structure, and therefore, it becomes possible to reduce a load to the damaged area of the articular cartilage (cartilage part under regeneration) and to effectively treat the articular cartilage damage. In other words, it becomes possible to obtain an external fixation device which includes a decreased number of parts and has a simple structure yet is capable of effectively treating the articular cartilage damage.

Preferably, the external fixation device further includes a second limiter portion disposed to connect the pair of first limiter portions to each other to limit movement of the first permanent magnet and the second permanent magnet in a third direction defined as a direction perpendicular to both of the first direction and the second direction. In this case, it becomes possible to limit movement of the first permanent magnet and the second permanent magnet in the third direction which is the direction perpendicular to both of the first direction and the second direction. This prevents the first permanent magnet and the second permanent magnet from becoming twisted to each other, thereby providing a smoother linear reciprocating relative movement between the first permanent magnet and the second permanent magnet.

Further preferably, the second limiter portion includes a magnetic member. In this case, the arrangement makes it possible to reduce a leakage magnetic field around the external fixation device. Therefore, the arrangement makes it possible to reduce adverse effect to the surrounds.

Further, preferably, the external fixation device includes a ball joint for attaching at least one of the first holding portion and the second holding portion to a corresponding one of the first pin and the second pin. In this case, at least one of the first holding portion and the second holding portion is attached to the corresponding pin(s) via the ball joint. Therefore, the arrangement allows simultaneous, relative stretching/contracting and pivoting movements between components on the first holding portion side and those on the second holding portion side of the external fixation device. Hence, the external fixation device is capable of following bending and stretching or pivoting movements of the joint, and the patient can move the joint freely. As a result, the joint can be moved smoothly, with a further reduced load onto the articular cartilage damage area (cartilage part under regeneration), making it possible to treat extensive articular cartilage damage more effectively.

Preferably, the second holding portion is connected to the ball joint, whereas, the first holding portion has a through-hole for insertion of the first pin. In this case, the first holding portion can be attached easily to the first pin by inserting the first pin through the through-hole of the first holding portion, and by attaching the second holding portion to the second pin via the ball joint, the joint can be moved smoothly.

Further preferably, at least one of the first holding portion and the second holding portion has a through-hole for insertion of the corresponding one of the first pin and the second pin. In this case, by inserting a corresponding pin(s), through the through-hole(s) of at least one of the first holding portion and the second holding portion, the holding portion is attached easily to the pin.

Further, preferably, the external fixation device includes a slanted sleeve fitted into the through-hole. In this case, by fitting the slanted sleeve into the through-hole of the holding portion, the pin which penetrates the through-hole is oriented in a slanted direction. Therefore, it is possible to insert the pin into an area of the bone portion which has a high density of bone, depending on specific conditions of individual patients.

Preferably, the pair of first limiter portions and the first holding portion are integral with each other. In this case, the arrangement further reduces the number of parts in the external fixation device.

Further preferably, each of the first permanent magnet and the second permanent magnet is rectangular parallelepiped. In this case, it is possible to obtain a large repulsion force with a simple shape at reduced cost.

According to another aspect of the present invention, there is provided a fixation device set which includes the above-described external fixation device for attaching to the first pin and the second pin on their common one end-side; and a pin fixture for attaching to the first pin and the second pin on their common another end-side. The pin fixture includes a fixture main body; a first connecting portion for connecting the fixture main body to the first pin; and a second connecting portion for connecting the fixture main body to the second pin.

According to the present invention, the external fixation device is attached to a common one end-side of the first pin which penetrates the first bone portion and the second pin which penetrates the second bone portion, whereas the pin fixture is attached to the other common end-side of the first pin and the second pin. The arrangement reduces unnecessary movement of the first pin and the second pin, thereby reducing damage to the bone portions. This works effectively, especially for patients having a low density of bone. As described, it becomes possible to obtain the fixation device set which includes a decreased number of parts and has a simple structure yet is capable effectively treating the articular cartilage damage.

Preferably, the first connecting portion is pivotable with respect to the fixture main body, whereas the second connecting portion is linearly movable with respect to the fixture main body. In this case, therefore, even if there happens to be variations in the position of the first pin and the second pin on the pin fixture side as viewed from the joint, it is possible to allow for such variations and keep holding the other end-side of the first pin and the second pin.

The above-described object and other objects, characteristics, aspects and advantages of the present invention will become clearer from the following detailed description of embodiments of the present invention to be made with reference to the attached drawings.

BRIEF DESCRIPTION OF DRAWINGS

FIG. 1(a) is a front view showing an external fixation device according to an embodiment of the present invention, whereas FIG. 1(b) is a side view thereof.

FIG. 2(a) is a front view showing the external fixation device in FIG. 1 with its second limiter portions removed, whereas FIG. 2(b) is a side view thereof.

FIG. 4(a) is a plan view showing a platy member, whereas FIG. 4(b) is a front view thereof.

FIG. 5(a) is a plan view showing a first support member, whereas FIG. 5(b) is a front view thereof.

FIG. 6(a) is a plan view showing a second support member, FIG. 6(b) is a front view thereof, and FIG. 6(c) is a bottom view thereof.

FIG. 8(a) is a front view showing a second shaft portion, whereas FIG. 8(b) is a side view thereof.

FIG. 9(a) is a front view showing a first platy portion, whereas FIG. 9(b) is a bottom view thereof.

FIG. 10(a) is a front view showing a second platy portion, whereas FIG. 10(b) is a bottom view thereof.

FIG. 11(a) is a front view showing an example of a pin fixture, whereas FIG. 11(b) is a side view thereof.

FIG. 16(a) shows a state where the knee is not bent, FIG. 16(b) shows a state where the knee is bent to 90°, and FIG. 16(c) shows a state where the knee is bent to a 120°.

FIG. 17(a) is a front view showing an external fixation device according to another embodiment of the present invention, whereas FIG. 17(b) is a side view thereof.

FIG. 18 (a) is a front view showing a slanted sleeve, whereas FIG. 18(b) is a side view thereof.

DESCRIPTION OF EMBODIMENTS

Hereinafter, embodiments of the present invention will be described with reference to the drawings.

Referring to FIG. 1 through FIG. 3, FIG. 17, and FIG. 20 through FIG. 31, in the embodiments of the present invention, a direction indicated by Arrow X, i.e., a direction of a repulsion force acting between a first permanent magnet and a second permanent magnet is the first direction; a direction indicated by Arrow Y, i.e., a direction perpendicular to Arrow X direction is the second direction; and a direction indicated by Arrow Z, i.e., a direction perpendicular to both of the directions indicated by Arrows X and Y is the third direction.

Figure 1:
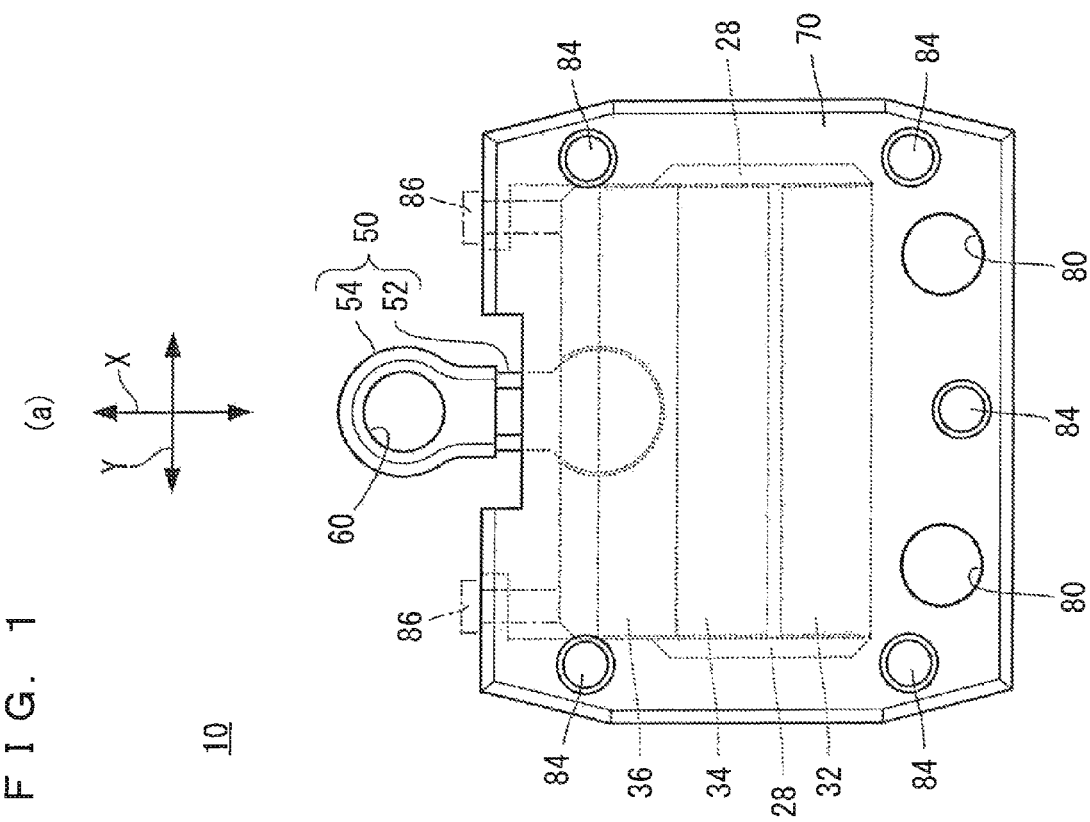
Figure 2:
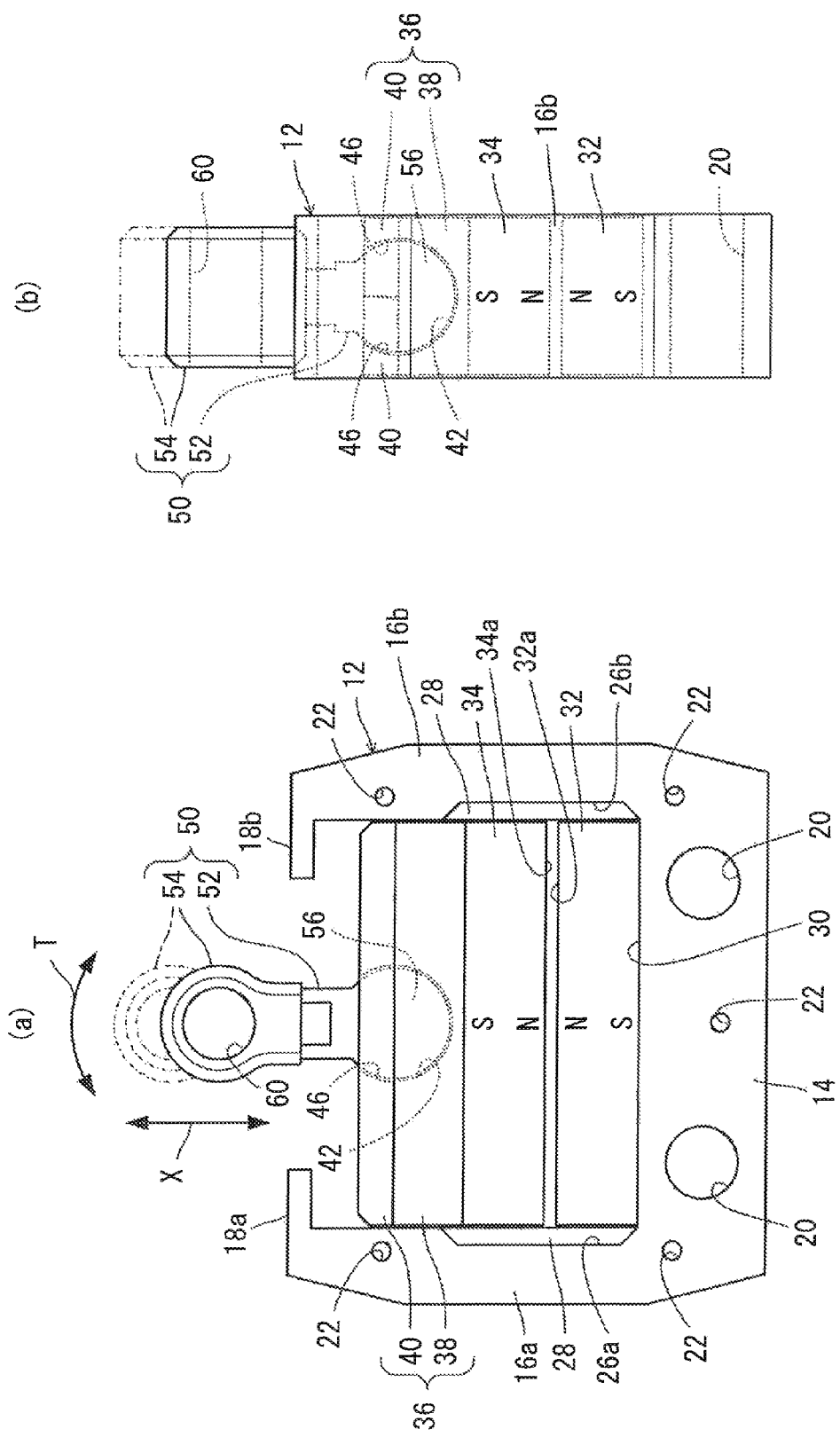
Figure 3:
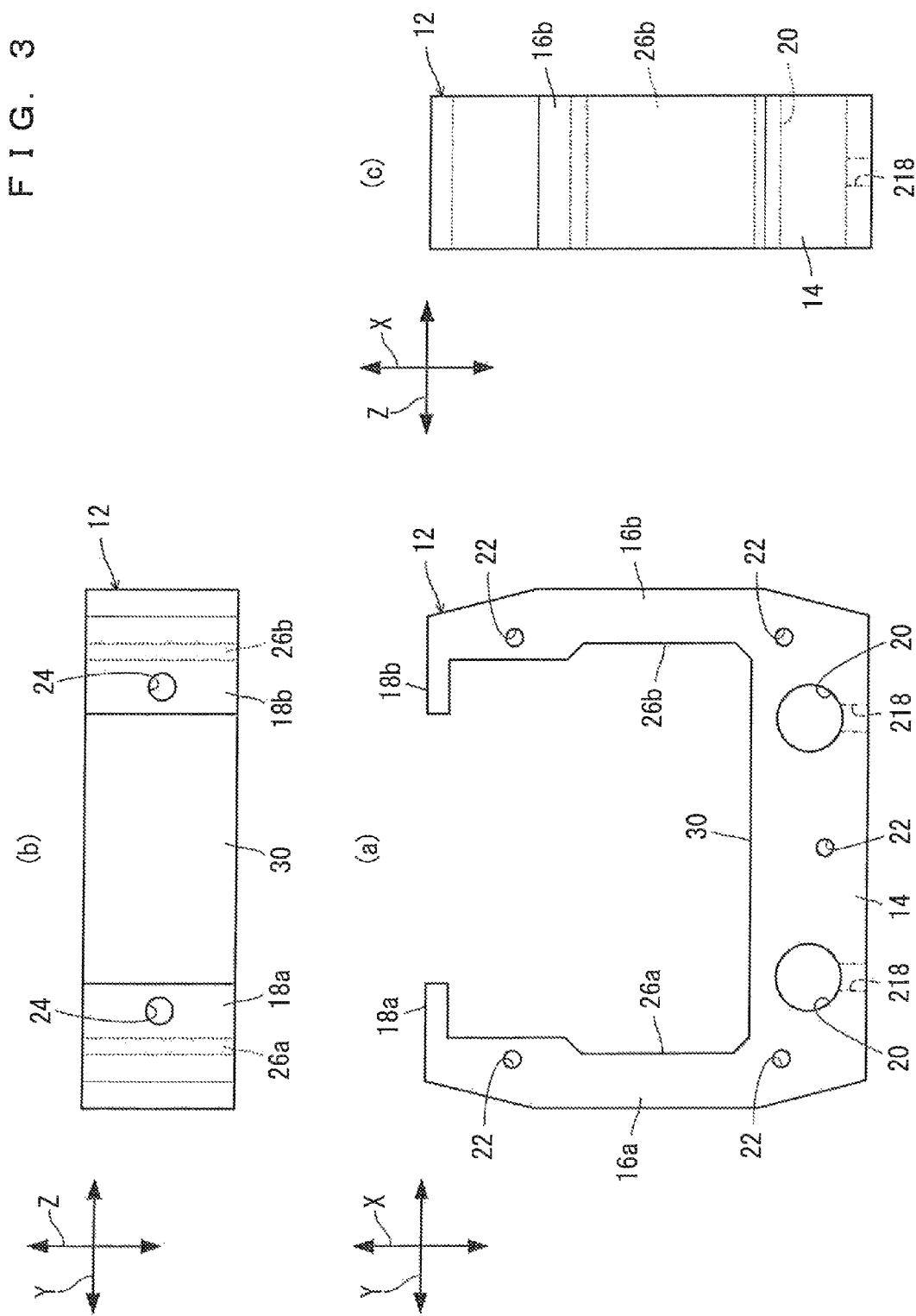
FIG. 3(a) is a front view showing a frame portion.
FIG. 3(b) is a plan view thereof.
FIG. 3(c) is a side view thereof.

Referring to FIG. 1 through FIG. 3, an external fixation device 10 includes a frame portion 12. The frame portion 12 opens in the first direction and the third direction, is substantially U-shaped, is magnetic, and preferably made of a ferrous material or a magnetic stainless steel such as SS400. The frame portion 12 includes a prismatic first holding portion 14; a pair of first limiter portions 16a, 16b which are substantially plate-like and extend from two ends of the first holding portion 14 in a substantially perpendicular direction with respect to the first holding portion 14; and stopper portions 18a, 18b formed at tips of the pair of first limiter portions 16a, 16b respectively. The first holding portion 14 has a plurality (two, in the present embodiment) of through-holes 20 extending in the third direction. The through-holes 20 will be penetrated by first pins P1 (to be described later). The frame portion 12 also has, in its two surfaces which are perpendicular to the third direction, a plurality (five in each surface, in the present embodiment) of screw holes 22 extending in the third direction. Further, each of the stopper portions 18a, 18b has a screw hole 24 penetrating in the first direction.

The first limiter portions 16a, 16b of the frame portion 12 sandwich a first permanent magnet 32 and a second permanent magnet 34 (both will be described later) from the second direction so as to allow the first permanent magnet 32 and the second permanent magnet 34 to move in the first direction but limit them in movement in the second direction.

As shown in FIG. 3, the first limiter portions 16a, 16b have their inner surfaces formed with recesses 26a, 26b respectively. Referring to FIG. 2, the recess 26a is fitted with a platy member 28, which is shown in FIG. 4, is substantially plate-like, and flush with the first limiter portion 16a, whereas the recess 26b is fitted with another platy member 28 flush with the first limiter portion 16b. The platy members 28 are nonmagnetic, preferably being formed of a nonmagnetic stainless steel such as SUS304, aluminum, titanium, etc. The platy members 28 prevent magnetic short-circuit between the first permanent magnet 32 and the second permanent magnet 34.

The first holding portion 14 of the frame portion 12 has an inner surface 30, to which the first permanent magnet 32 is attached. In other words, the first holding portion 14 is on a surface away from an opposing surface 32a of the first permanent magnet 32. Between the first limiter portions 16a, 16b of the frame portion 12, there is disposed the second permanent magnet 34 to oppose to the first permanent magnet 32. The first permanent magnet 32 and the second permanent magnet 34 have the same shape of a generally rectangular parallelepiped, and are disposed so that their same poles oppose to each other. As shown in FIG. 2, in the present embodiment, the first permanent magnet 32 has its N pole on the opposing surface 32a side, and its S pole on the side away from the opposing surface 32a (the first holding portion 14 side). Likewise, the second permanent magnet 34 has its N pole on its opposing surface 34a side, and its S pole on the side away from the opposing surface 34a (on the side facing a second holding portion 36 (which will be described later)). The first permanent magnet 32 and the second permanent magnet 34 are provided preferably by an R—Fe—B sintered magnet (R represents a rare-earth element).

The second holding portion 36 is on a surface away from the opposing surface 34a of the second permanent magnet 34. The second holding portion 36 includes a strip-shaped first support member 38 as shown in FIG. 5, and two second support members 40 as split halves as shown in FIG. 6. The first support member 38 has a hemispherical recess 42, and a plurality (eight, in the present embodiment) of screw holes 44. The second support member 40 has a semicircular recess 46, and a plurality (four, in the present embodiment) of screw holes 48 as through holes. The first support member 38 and the second support members 40 are magnetic, formed preferably of a ferrous material or a magnetic stainless steel such as SS400.

Figure 7:
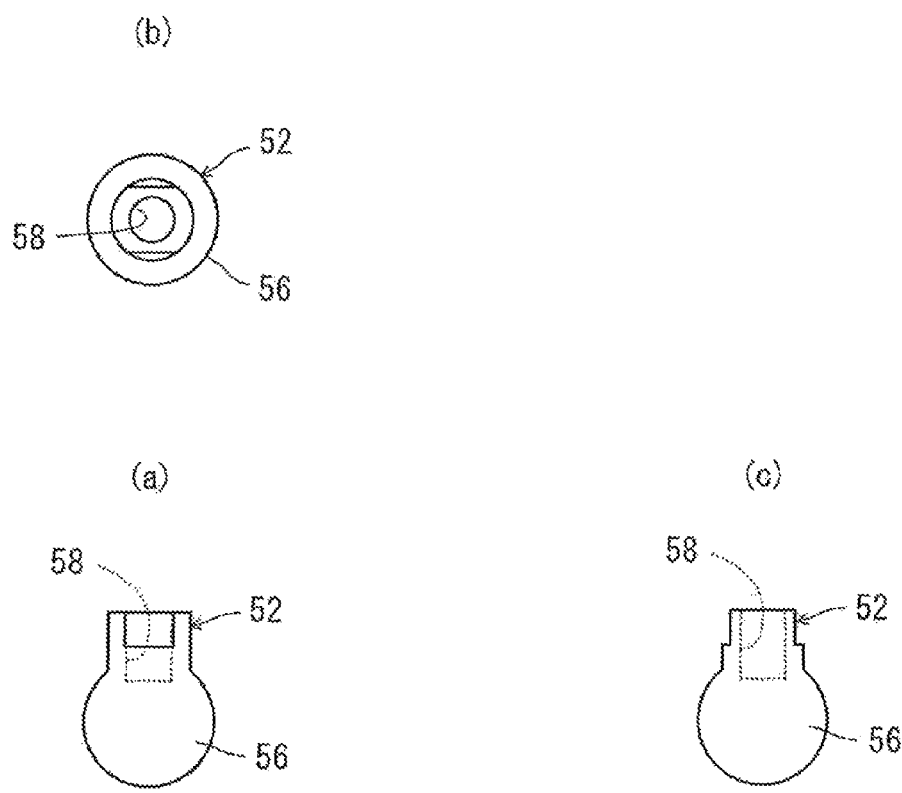
FIG. 7(a) is a front view showing a first shaft portion.
FIG. 7(b) is a plan view thereof.
FIG. 7(c) is a side view thereof.
Figure 8:
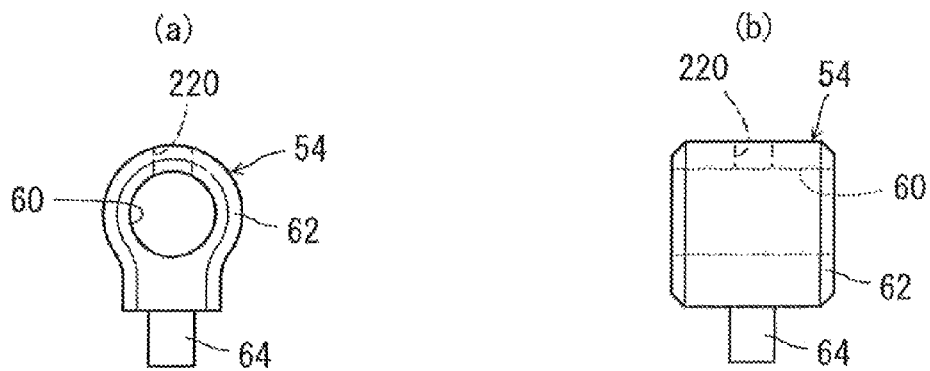

As shown in FIG. 1 and FIG. 2, the second holding portion 36 is connected to a ball joint 50. The ball joint 50 includes a first shaft portion 52 and a second shaft portion 54. Referring to FIG. 7, the first shaft portion 52 has a ball portion 56 and a female-threaded portion 58. Referring to FIG. 8, the second shaft portion 54 has a tube-like portion 62 which has a through-hole 60; and a male-threaded portion 64. The first shaft portion 52 and the second shaft portion 54 are nonmagnetic, preferably being formed of a nonmagnetic stainless steel such as SUS304, aluminum, titanium, etc. The through-hole 60 will be penetrated by a second pin P2 (to be described later). As the male-threaded portion 64 is threaded into the female-threaded portion 58, the ball joint 50 is completed as an assembly. The ball portion 56 of the ball joint 50 is inserted into the recess 42 in the first support member 38 of the second holding portion 36, and then the first support member 38 and the two second support members 40 are assembled together to surround an exposed region of the ball portion 56 with two recesses 46. Under this state, screws (not illustrated) are threaded into the screw holes 48, 44.

Returning to FIG. 1, two second limiter portions 66 are disposed to cover two openings of the frame portion 12 opening in the third direction. In other words, in order to limit the first permanent magnet 32 and the second permanent magnet 34 from moving in the third direction, the two second limiter portions 66 are placed, connecting the pair of first limiter portions 16a, 16b to each other. Each second limiter portion 66 includes a first platy portion 68 and a second platy portion 70. Referring to FIG. 9 and FIG. 10, the first platy portion 68 and the second platy portion 70 have substantially the same shape except for their thicknesses. The first platy portion 68 has a cutout 72; a plurality (two, in the present embodiment 2) of through-holes 74; and a plurality (five, in the present embodiment) of screw holes 76 as through-holes. The first platy portion 68 is nonmagnetic, preferably being formed of a nonmagnetic stainless steel such as SUS304, aluminum, titanium, etc. The second platy portion 70 has a cutout 78; a plurality (two, in the present embodiment) of through-holes 80; and a plurality (five, in the present embodiment) of screw holes 82 as through-holes. The second platy portion 70 is magnetic, and preferably formed of a ferrous material such as SS400, or a magnetic stainless steel.

The frame portion 12 is sandwiched from the third direction by the two first platy portions 68 to cover two openings of the frame portion 12 opening in the third direction; the second platy portions 70 are placed on the respective first platy portions 68; and then screws 84 (see FIG. 1) are threaded into the screw holes 82, 76, 22, whereby the first platy portions 68 and the second platy portions 70 are attached to the frame portion 12.

Referring to FIG. 2, according to the external fixation device 10 as described, the second permanent magnet 34, and therefore the ball joint 50, is movable linearly in a reciprocating fashion in the first direction, whereas the ball joint 50 is pivotable (for example, in Arrow T direction) around the ball portion 56 with respect to the second holding portion 36. Thus, when the external fixation device 10 is attached to a joint via the first pins P1 and the second pin P2, the external fixation device 10 can allow the joint to move in a direction in which the first pins P1 become twisted with respect to the second pin P2.

Returning to FIG. 1 and FIG. 3, until the external fixation device 10 as described thus far is attached to a joint, set screws 86 which are threaded into the two screw holes 24 keep the second holding portion 36 and the second permanent magnet 34 pressed toward the first permanent magnet 32.

Next, the pin fixture 100 will be described with reference to FIG. 11 through FIG. 14.

Figure 11:
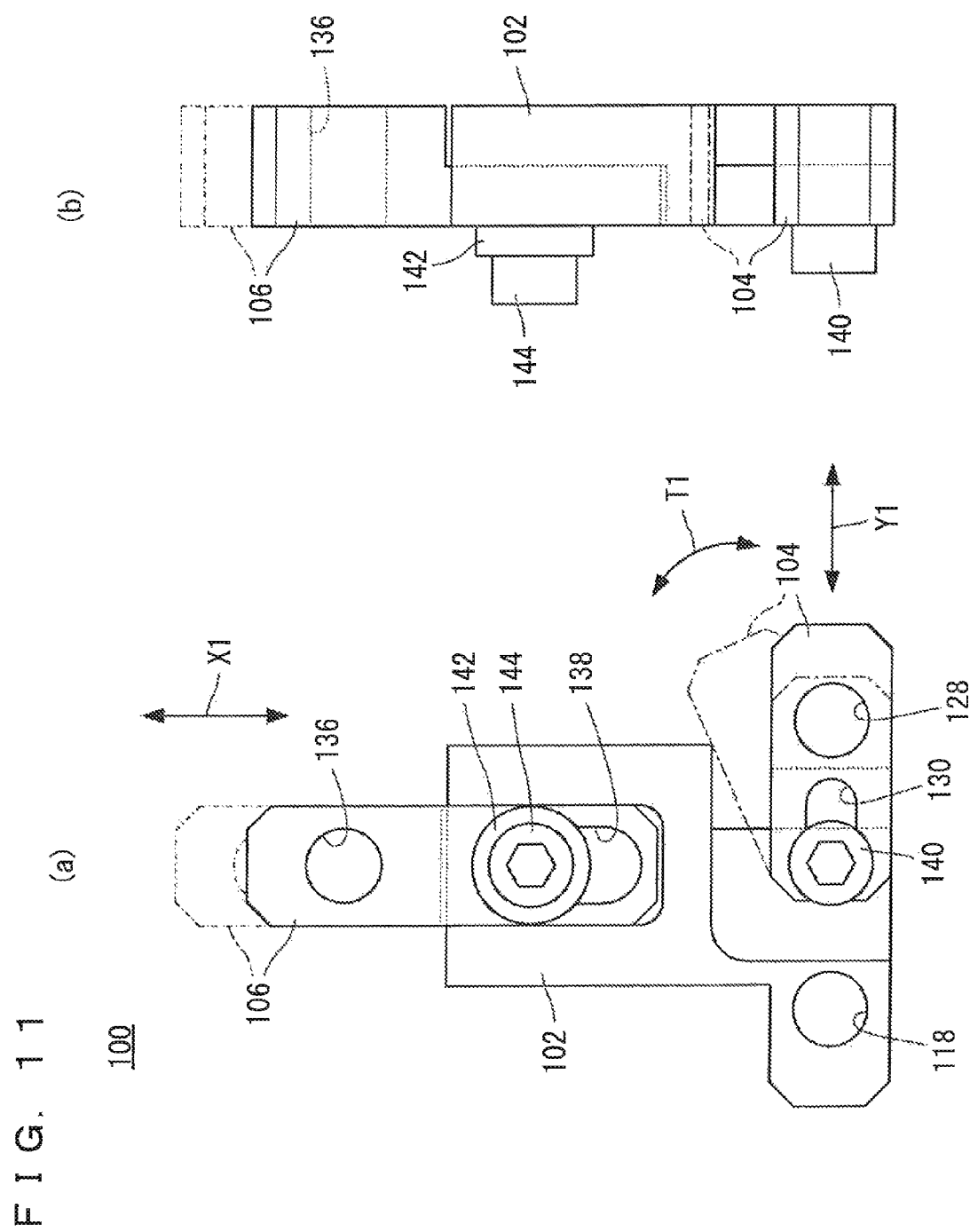

As shown in FIG. 11, the pin fixture 100 includes a fixture main body 102; a first connecting portion 104 which connect the fixture main body 102 and the first pin P1 (see FIG. 15) to each other; and a second connecting portion 106 which connects the fixture main body 102 and the second pin P2 (see FIG. 15) to each other. The fixture main body 102, the first connecting portion 104 and the second connecting portion 106 are nonmagnetic, preferably being formed of a nonmagnetic stainless steel such as SUS304, aluminum, titanium, etc.

Figure 12:
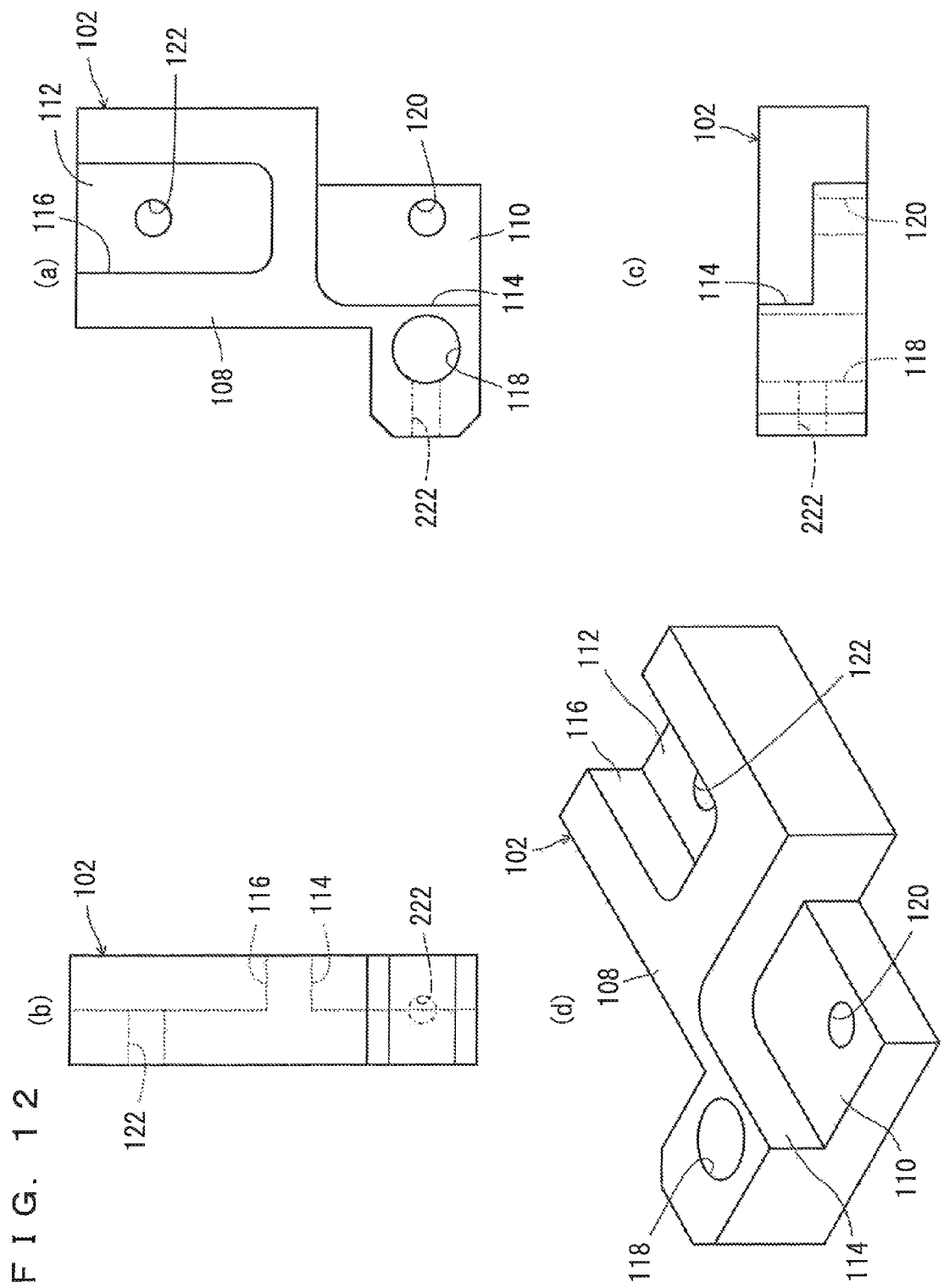
FIG. 12(a) is a front view showing a fixture main body.
FIG. 12(b) is a side view thereof.
FIG. 12(c) is a bottom view thereof.
FIG. 12(d) is a perspective view thereof.

As shown in FIG. 12, the fixture main body 102 is substantially J-shaped in a front view (see FIG. 12(a)), and includes a thick portion 108, and two thin portions 110, 112. The thin portion 110 is obtained by forming a recess 114 in the fixture main body 102. The thin portion 112 is obtained by forming a recess 116 opening in one direction in the fixture main body 102. The thick portion 108 is formed with a through-hole 118, the thin portion 110 is formed with a screw hole 120 as a through-hole, and the thin portion 112 is formed with a screw hole 122 as a through-hole.

Figure 13:
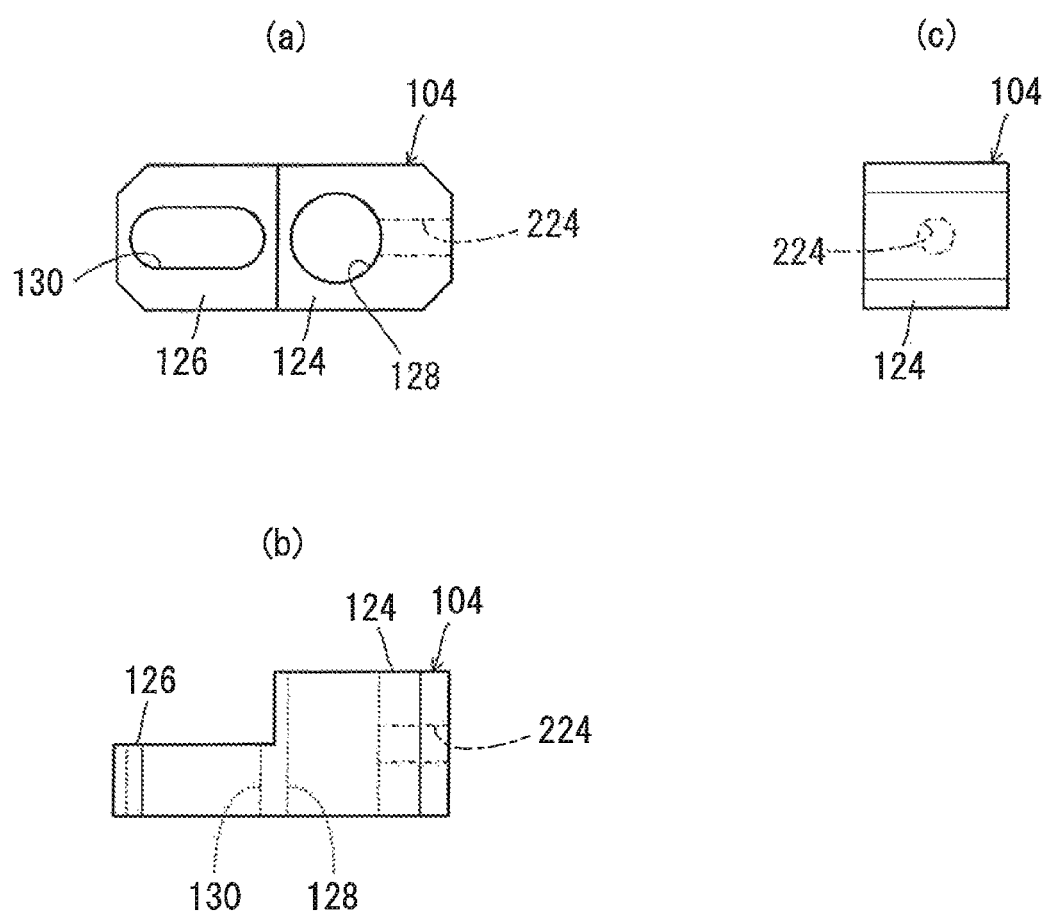
FIG. 13(a) is a front view showing a first connecting portion.
FIG. 13(b) is a bottom view thereof.
FIG. 13(c) is a side view thereof.

As shown in FIG. 13, the first connecting portion 104 is substantially I-shaped in a front view (see FIG. 13(a)), and includes a thick portion 124 and a thin portion 126. The thick portion 124 is formed with a through-hole 128, whereas the thin portion 126 is formed with a through-hole 130 as a long hole.

Figure 14:
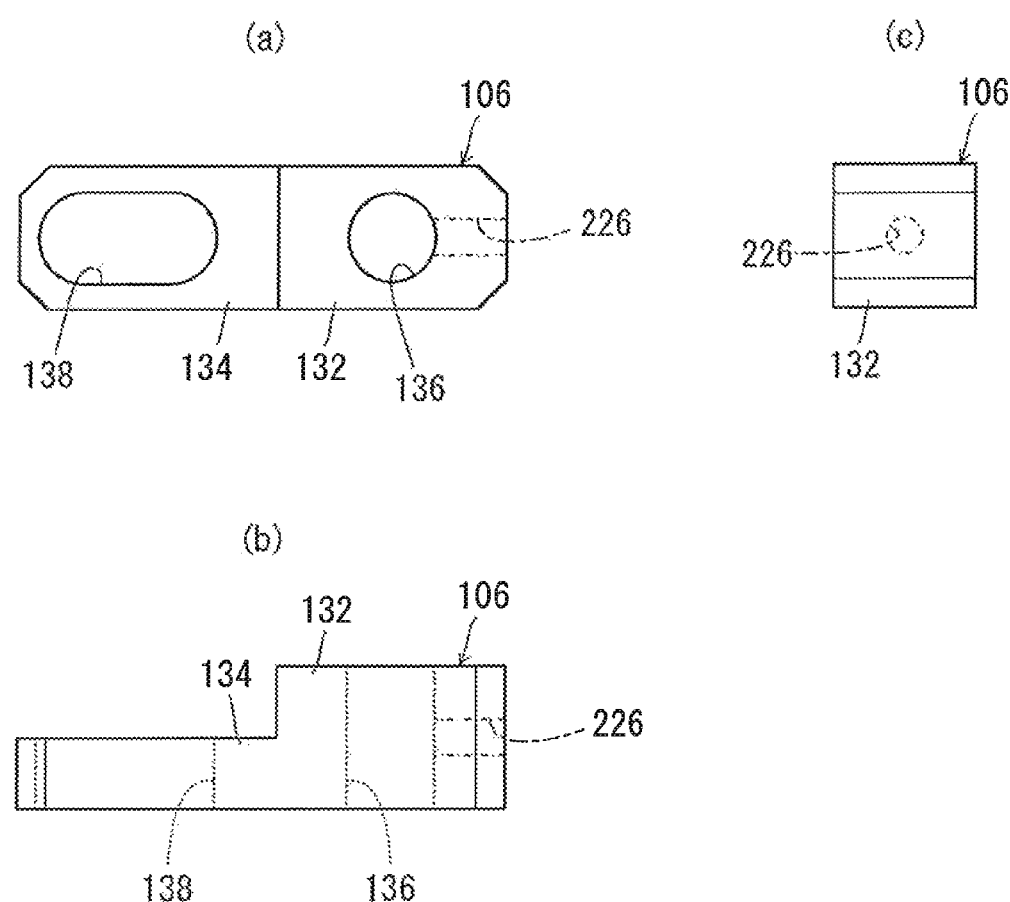
FIG. 14(a) is a front view showing a second connecting portion.
FIG. 14(b) is a bottom view thereof.
FIG. 14(c) is a side view thereof.

As shown in FIG. 14, the second connecting portion 106 is substantially I-shaped in a front view (see FIG. 14(a)), and includes a thick portion 132 and a thin portion 134. The thick portion 132 is formed with a through-hole 136, whereas the thin portion 134 is formed with a through-hole 138 as a long hole.

Referring to FIG. 11 through FIG. 13, the screw hole 120 of the fixture main body 102 and the through-hole 130 of the first connecting portion 104 align with each other when the thin portion 126 of the first connecting portion 104 is disposed in the recess 114 of the fixture main body 102, and under this state a bolt 140 is inserted through the through-hole 130 and threaded into the screw hole 120. Being attached as described, the first connecting portion 104 is pivotable in a direction indicated by Arrow T1 within an angle range of approximately 140 degrees and is linearly movable in a direction indicated by Arrow Y1, with respect to the fixture main body 102. In regard of the pivotal movement of the first connecting portion 104, it is acceptable in actual use, that as far as the first connecting portion 104 is pivotable with respect to the fixture main body 102 within a ± approximately 25-degree range from a position indicated by solid lines in FIG. 11(a). Further, referring to FIG. 14, the screw hole 122 of the fixture main body 102 and the through-hole 138 of the second connecting portion 106 align with each other when the thin portion 134 of the second connecting portion 106 is fitted into the recess 116 of the fixture main body 102, and under this state a washer 142 is placed in between, a bolt 144 is inserted through the through-hole 138, and threaded into the screw hole 122. Being attached as described, the second connecting portion 106 is linearly movable with respect to the fixture main body 102 in a direction indicated by Arrow X1.

Figure 15:
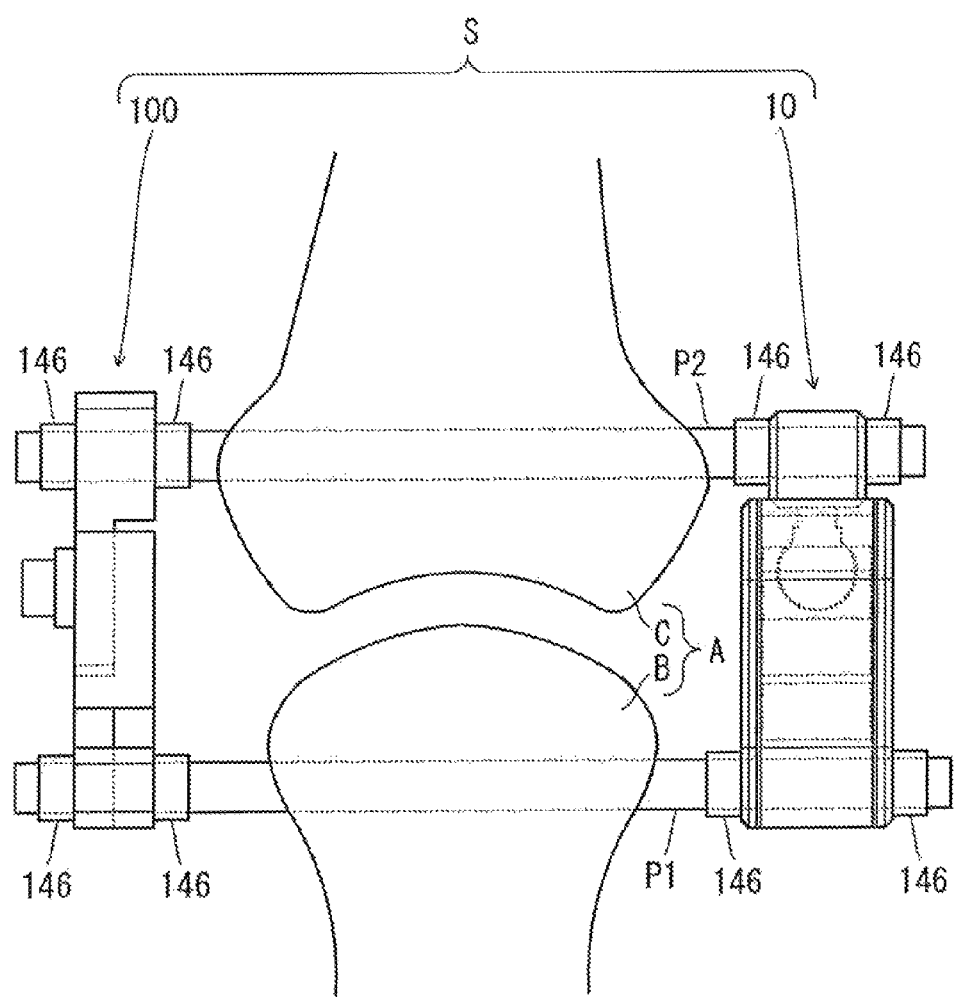
FIG. 15 is an illustrative drawing showing a fixation device set, with an external fixation device attached on one side of a knee joint, and a pin fixture attached to the other side thereof.

Referring to FIG. 15, a fixation device set S which includes the external fixation device 10 and the pin fixture 100 is attached to a joint as follows: Herein, description will be made for a case where a first bone portion B on a lower-leg portion side and a second bone portion C on a thigh side are separated from each other, and under this condition, the external fixation device 10 and the pin fixture 100 are attached to a knee joint A to sandwich the knee joint in between so that the external fixation device 10 is on one side of the first bone portion B and the second bone portion C, whereas the pin fixture 100 is on the other side of the first bone portion B and the second bone portion C.

First, by means of a drill for example, two through-holes are made in the first bone portion B, and one through-hole as well, in the second bone portion C. Next, the first pins P1 are inserted through the through-holes made in the first bone portion B respectively, whereas the second pin P2 is inserted through the through-hole made in the second bone portion C. It is preferable that each of the first pins P1 and the second pin P2 is formed in a rod-like shape, using a material containing titanium which has superb biocompatibility. In the present embodiment, each of the first pins P1 and the second pin P2 has their two end portions formed with a male-thread on their outer surface. FIG. 15 shows only one of the two first pins P1.

Then, three nuts 146, the external, fixation device 10 shown in FIG. 1, and three nuts 146 are attached in this order to the three pins (two first pins P1 and one second pin P2) on one side as viewed from the knee joint A. In other words, on one side as viewed from the knee joint A, a nut 146 is advanced along each of the two first pins P1 and one second pin P2, to an inner side (side closer to the knee joint A); each of the first pins P1 is inserted through corresponding through-holes (through-holes 20, 74, 80) of the external fixation device 10, while the second pin P2 is inserted through the through-hole 60 in the ball joint 50 of the external fixation device 10, whereby the external fixation device 10 is inserted around the three pins; and further, a nut 146 is inserted around each of the two first pins P1 and the second pin P2. Hence, the external fixation device 10 is attached to the two first pins P1 and one second pin P2, being sandwiched from two sides by three nuts 146 each on each side. Under this state, the external fixation device 10 is held so as not to come out of the first pins P1 and the second pin P2. Each of the first pins P1 and the second pin P2 is rotatable with respect to the external fixation device 10. However, the first pins P1 may be non-rotatable with respect to the external fixation device 10.

Thereafter, as shown in FIG. 1, the two set screws 86 which keep the second holding portion 36 and the second permanent magnet 34 pressed toward the first permanent magnet 32 are released or removed, as necessary, from the external fixation device 10. As a result, due to a repulsion force acting between the first permanent magnet 32 and the second permanent magnet 34, a force works in a direction to increase a distance between the first pins P1 and the second pin P2.

This expansion/contraction movement of the external fixation device 10 is observed, to determine if the pin fixture 100 should be attached, another external fixation device 10 should be attached, or nothing should be made, on the other side as viewed from the knee joint A.

In the present description, the pin fixture 100 will be attached.

The pin fixture 100 is attached in the same way as the external fixation device 10.

First, three nuts 146, the pin fixture 100 shown in FIG. 11, and three nuts 146 are attached in this order to the three pins (two first pins P1 and one second pin P2) on the other side as viewed from the knee joint A. In other words, on the other side as viewed from the knee joint A, a nut 146 is advanced along each of the two first pins P1 and one second pin P2, to an inner side (side closer to the knee joint A); each of the first pins P1 is inserted through a corresponding one of the through-holes 118, 128 of the pin fixture 100 while the second pin P2 is inserted through the through-hole 136 in the pin fixture 100, whereby the pin fixture 100 is inserted around the three pins; and further, a nut 146 is inserted around each of the two first pins P1 and the second pin P2. Hence, the pin fixture 100 is attached to the two first pins P1 and one second pin P2, being sandwiched from two sides by three nuts 146 each on each side. Under this state, the pin fixture 100 is held so as not to come out of the first pins P1 and the second pin P2. Each of the first pins P1 and the second pin P2 is rotatable with respect to the pin fixture 100. However, the first pins P1 may be non-rotatable with respect to the pin fixture 100.

In the external fixation device 10 attached to the knee joint A, when the patient is standing upright for example, a repulsion force of approximately 240N (24.5 kgf) is acting between the first permanent magnet 32 and the second permanent magnet 34.

Description will be made for a case where a knee is being bent with the external fixation device 10 and the pin fixture 100 attached thereto as described above, with reference to FIG. 16(*a*) through FIG. 16(*c*).

Figure 16:
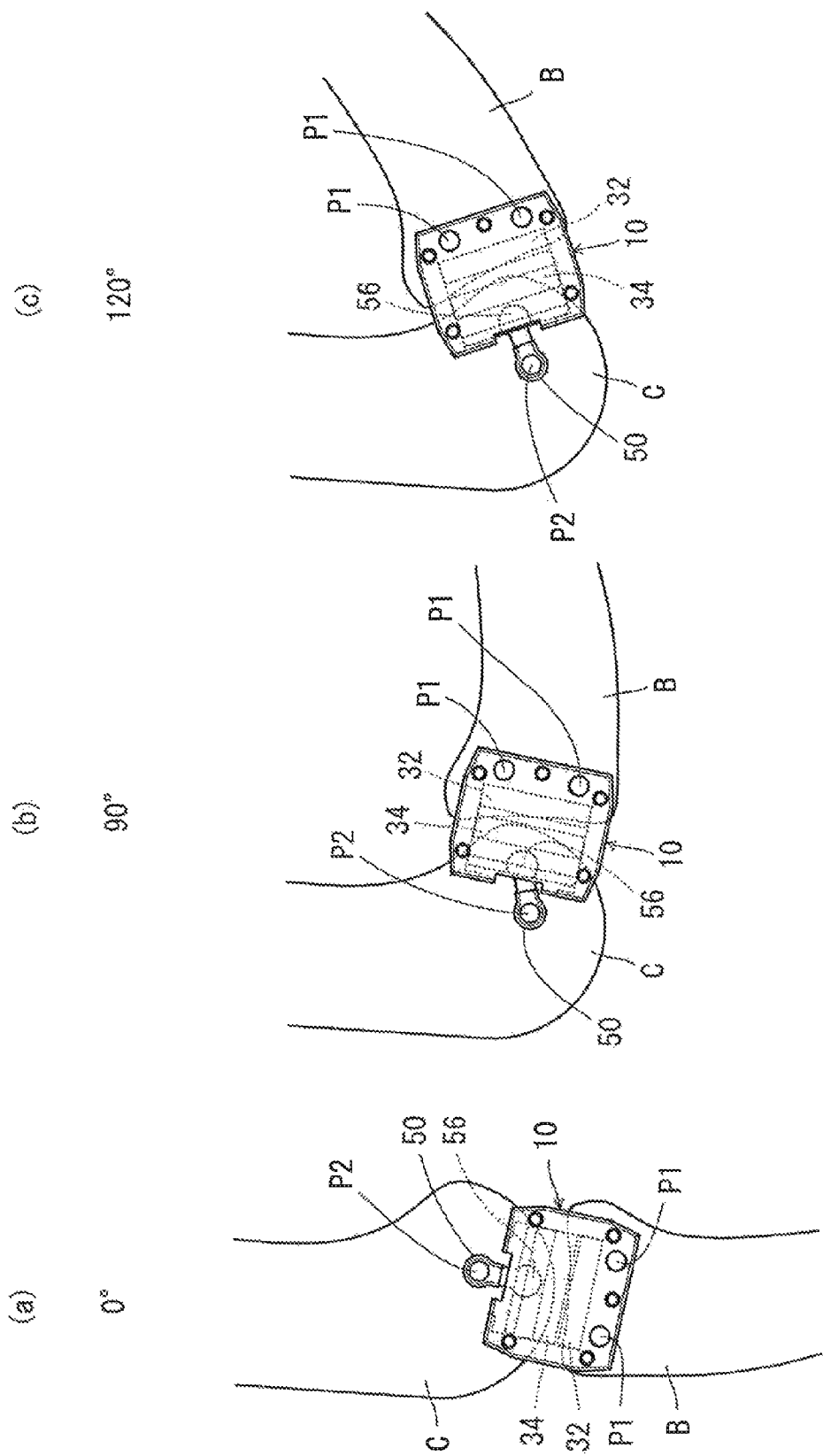
FIG. 16 is an illustrative drawing showing a knee joint and the external fixation device when the knee is bent.

As shown in FIG. 16(*a*), when the knee is not bent, the first permanent magnet 32 and the second permanent magnet 34 are close to each other. Next, when the knee is bent at approximately 90° as shown in FIG. 16(*b*), the second permanent magnet 34 moves away from the first permanent magnet 32. Then, when the knee is bent at approximately 120° as shown in FIG. 16(*c*), the second permanent magnet 34 moves further away from the first permanent magnet 32. While the knee is being bent from 0° (stretched state) to 120°, the ball joint 50 pivots around the ball portion 56 with respect to the second holding portion 36. As described, the first bone portion B and the second bone portion C are kept apart from each other when the knee is bent.

According to the external fixation device 10, the first permanent magnet 32 and the second permanent magnet 34 are disposed so that their same poles oppose to each other, and the first permanent magnet 32 and the second permanent magnet 34 are sandwiched between the pair of first limiter portions 16*a*, 16*b*. Therefore, the first permanent magnet 32 and the second permanent magnet 34 repulse against each other, moving away from each other in the direction of the repulsion force, i.e., in the first direction. As a result, the first pins P1 which are connected to the first permanent magnet 32 via the first holding portion 14, and the second pin P2 which is connected to the second permanent magnet 34 via the second holding portion 36 move away from each other, making it possible to move the knee joint A while the first bone portion B and the second bone portion C are kept apart from each other, i.e., with the cartilage part of the knee joint A kept open. By utilizing the repulsion force between the first permanent magnet 32 and the second permanent magnet 34 as described above, it becomes possible to reduce the number of parts and simplify the structure, and therefore, it becomes possible to reduce a load to the damaged area of the articular cartilage (cartilage part under regeneration) and to effectively treat the articular cartilage damage. In other words, it becomes possible to obtain the external fixation device 10 which includes a decreased number of parts and has a simple structure yet is capable of effectively treating the articular cartilage damage. Since the external fixation device 10 can be made at a low cost, made smaller and more compactly than conventional ones, it can reduce burdens on the patient in daily life.

By providing two second limiter portions 66 to connect the pair of first limiter portions 16a, 16b to each other, it becomes possible to limit movement of the second permanent magnet 34 in the third direction which is the direction perpendicular to both of the first direction and the second direction, preventing the first permanent magnet 32 and the second permanent magnet 34 from becoming twisted to each other, thereby providing a smoother linear reciprocating movement of the second permanent magnet 34 relative to the first permanent magnet 32. Since the first permanent magnet 32 and the second permanent magnet 34 stay inside a space surrounded by the frame portion 12 and the second limiter portions 66, neither the first permanent magnet 32 nor the second permanent magnet 34 will rub against or pinch the patient's skin.

The second limiter portions 66 include the second platy portions 70 which are magnetic. This reduces a leakage magnetic field around the external fixation device 10. Therefore the arrangement reduces adverse effect to the surrounds.

The second holding portion 36 is attached to the second pin P2 via the ball joint 50. This allows simultaneous, relative stretching/contracting (linear) and pivoting movements between components on the first holding portion 14 side and those on the second holding portion 36 side of the external fixation device 10. Therefore, the external fixation device 10 is capable of following bending/stretching or pivoting movements of the knee joint A, and the patient can move the knee joint A freely. As a result, the knee joint A can be moved smoothly, with a further reduced load onto the articular cartilage damage area (cartilage part under regeneration), making it possible to treat extensive articular cartilage damage more effectively.

The arrangement that the first pins P1 are inserted through the through-holes 20 in the first holding portion 14 makes it easy to attach the first holding portion 14 to the first pins P1.

The pair of first limiter portions 16a, 16b and the first holding portion 14 are formed integrally with each other. This further reduces the number of parts of the external fixation device 10.

Each of the first permanent magnet 32 and the second permanent magnet 34 is rectangular parallelepiped, so a large repulsion force can be obtained with a simple shape at reduced cost.

The second pin P2 is rotatable with respect to the external fixation device 10. This makes it possible to move the knee joint A more freely.

The first bone portion B is penetrated by the first pins P1 and the second bone portion C is penetrated by the second pin P2, and the external fixation device 10 is attached on one end-side of the first pins P1 and the second pin P2, whereas the pin fixture 100 is attached on the other end-side thereof. This reduces unnecessary movement of the first pins P1 and the second pin P2, thereby reducing damage to the first bone portion B and the second bone portion C. This works effectively, especially for patients having a low density of bone. As described, it becomes possible to obtain the fixation device set S which includes a decreased number of parts and has a simple structure yet is capable effectively treating the articular cartilage damage.

Figure 17:
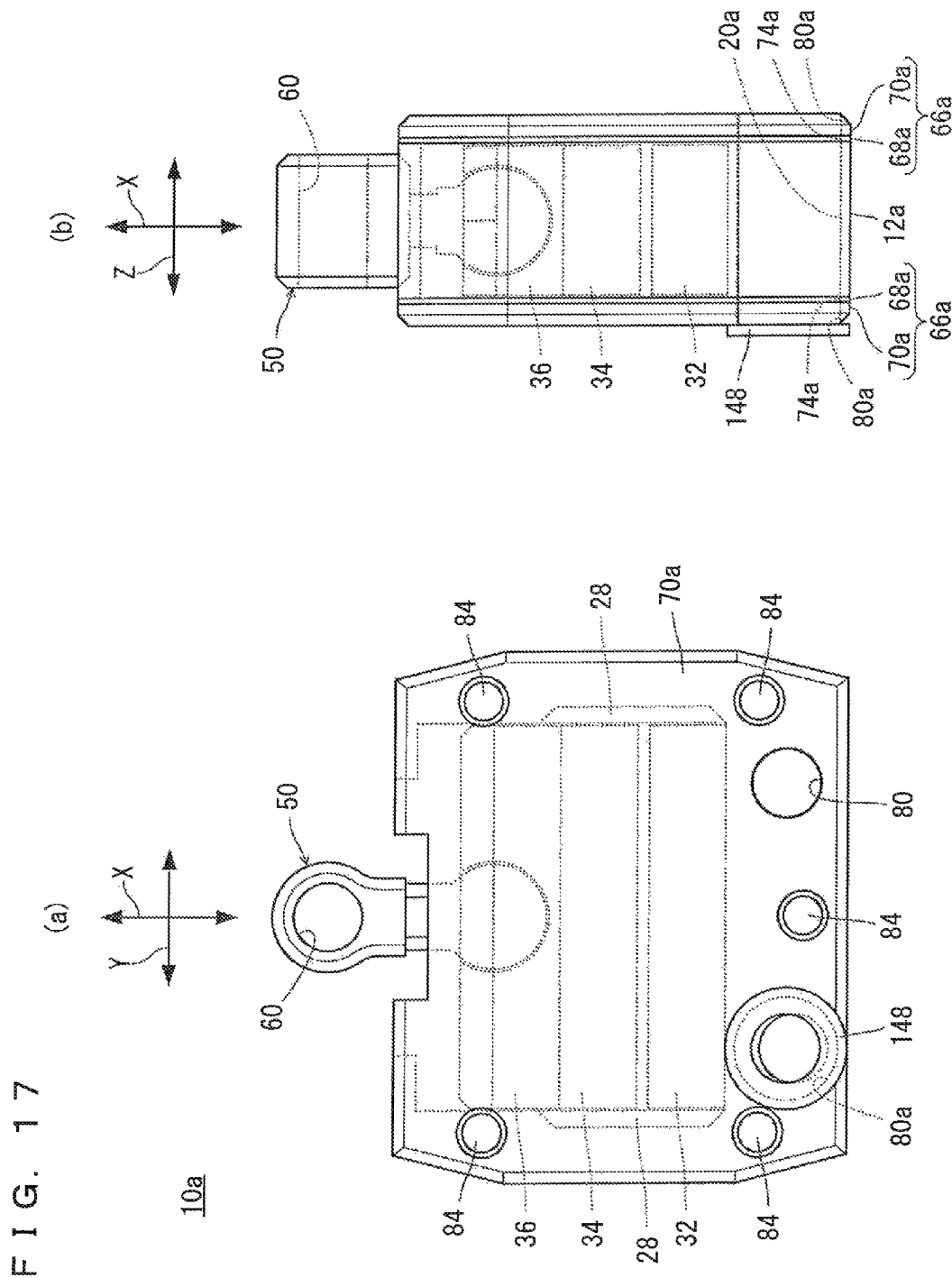

FIG. 17 shows an external fixation device 10a according to another embodiment.

The external fixation device 10a has an attachable/detachable slanted sleeve 148. Also, the external fixation device 10a has a frame portion 12a, which has the through-hole 20 and a through-hole 20a having a greater diameter than the diameter of the through-hole 20, as through-holes for insertion of the first pins P1. Accordingly, the first platy portion 68a of the second limiter portion 66a have the through-hole 74 and a through-hole 74a which has a greater diameter than the diameter of the through-hole 74, whereas the second platy portion 70a of the second limiter portion 66a has the through-hole 80 and a through-hole 80a which has a greater diameter than the diameter of the through-hole 80. The external fixation device 10a has through-holes 20, 74 and 80, each having the same diameter as the respective diameter of the through-holes 20, 74 and 80 in the external fixation device 10. Specifically, using FIG. 17(a) as an example, the through-holes 20a, 74a and 80a are on the left side, whereas the through-holes 20, 74 and 80 are on the right side.

Figure 18:
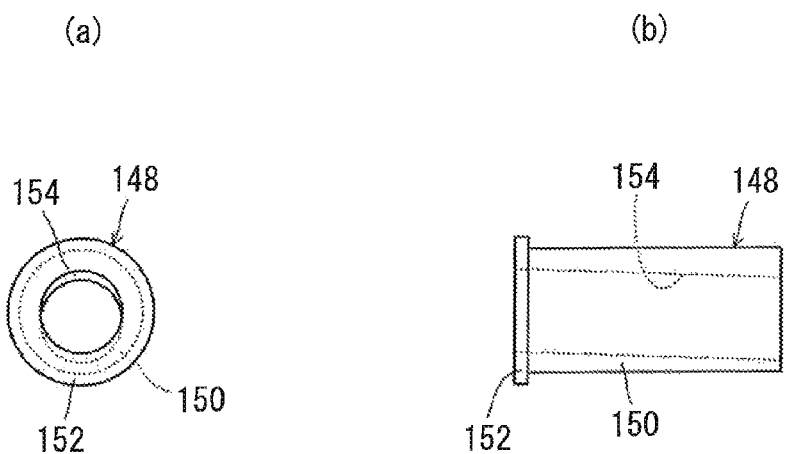

Referring to FIG. 18, the slanted sleeve 148 has a cylindrical portion 150, and an annular flange portion 152 formed at an end of the cylindrical portion 150. The cylindrical portion 150 and the flange portion 152 are formed with a through-hole 154 which extends in a direction slightly slanted with respect to an axis of the cylindrical portion 150 and flange portion 152. The slanted sleeve 148 as described is fitted into the through-holes 80a of the second platy portions 70a, the through-holes 74a of the first platy portions 68a, and the through-hole 20a of the frame portion 12a. The through-hole 154 will be penetrated by the first pin P1. The slanted sleeve 148 is nonmagnetic, preferably being formed of a nonmagnetic stainless steel such as SUS304, aluminum, titanium, etc. Other arrangements are the same as in the external fixation device 10, so description therefor will not be repeated.

According to the external fixation device 10a as described, the slanted sleeve 148 is fitted into the through-holes 80a, 74a and 20a, and therefore it is possible to orient the first pin P1 which is inserted through the through-hole 154 in a slanted direction. This means that it is possible to insert the first pin P1 into an area of the first bone portion B which has a high density of bone, depending on specific conditions of individual patients.

The first connecting portions 104 is pivotable with respect to the fixture main body 102, and the second connecting portion 106 is linearly movable with respect to the fixture main body 102. Therefore, even if there happens to be variations in the position of the first pins P1 and the second pin P2 on the pin fixture 100 side as viewed from the knee joint A, it is possible to allow for such variations and keep holding the other end-side of the first pins P1 and the second pin P2.

Figure 19:
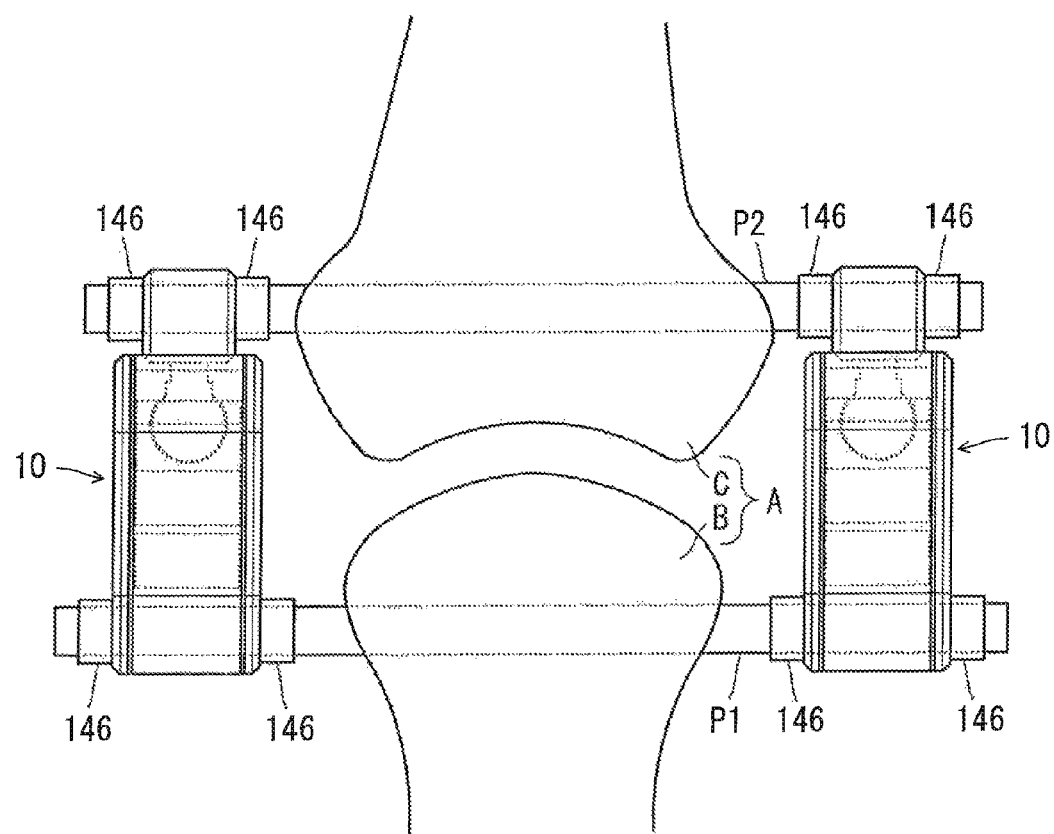
FIG. 19 is an illustrative drawing showing a state where the external fixation devices are attached on both sides of a knee joint.

As shown in FIG. 19, there may be an arrangement where the pin fixture 100 is not used, and two of the external fixation devices 10 are attached on two sides of the knee joint A. In this case, it is not necessary to prepare the pin fixture 100.

Figure 20:
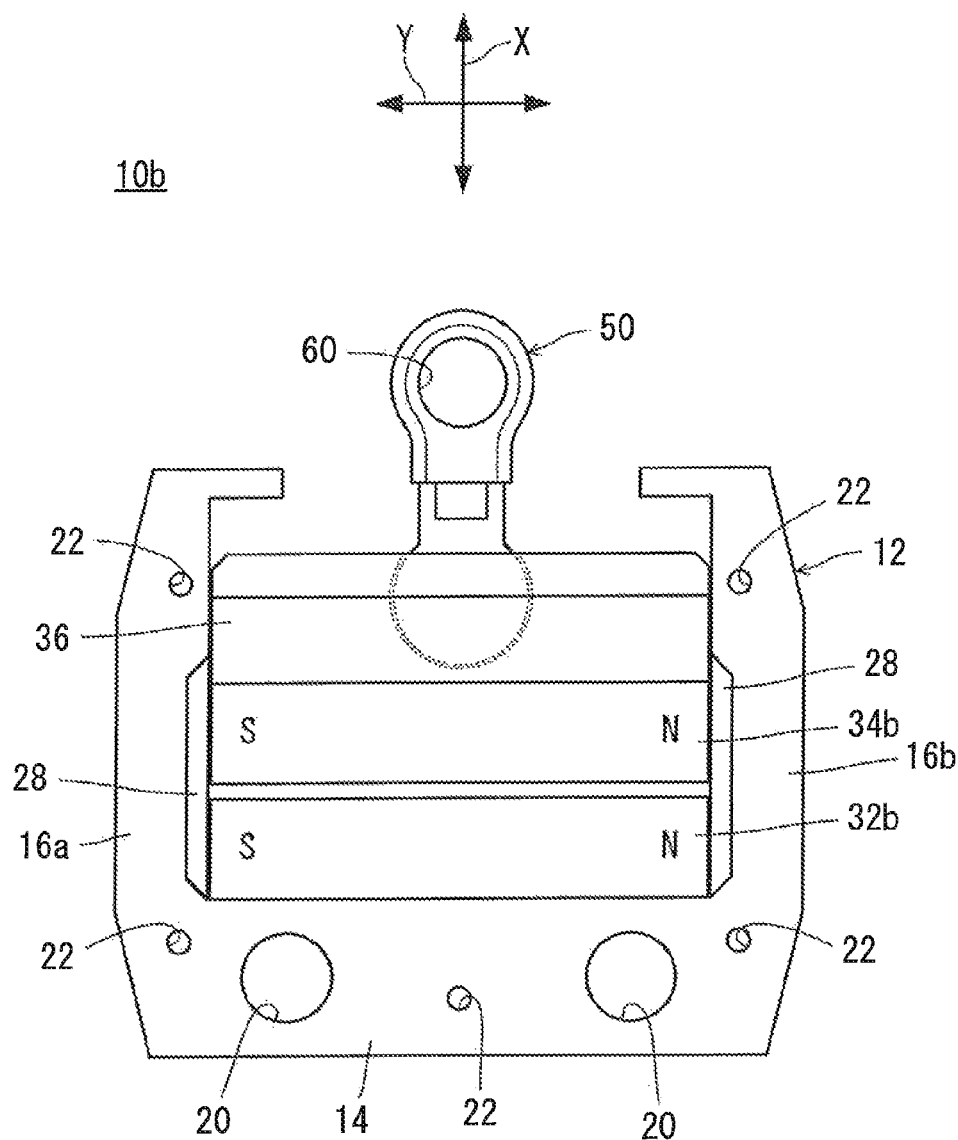
FIG. 20 is a front view showing an external fixation device according to still another embodiment of the present invention.

Like an external fixation device 10b shown in FIG. 20, a first permanent magnet 32b and a second permanent magnet 34b may be disposed in such a fashion that their N poles oppose to each other and their S poles oppose to each other. Other arrangements are the same as in the external fixation device 10, so description therefor will not be repeated. It should be noted here that in FIG. 20 and thereafter, when an external fixation device is shown, the second limiter portions will not be described in order to avoid complication of the drawing. However, the second limiter portions are included, with appropriate modifications made thereto in accordance with the corresponding external fixation device.

The external fixation device 10b as described provides the same advantages as offered by the external fixation device 10.

Figure 21:
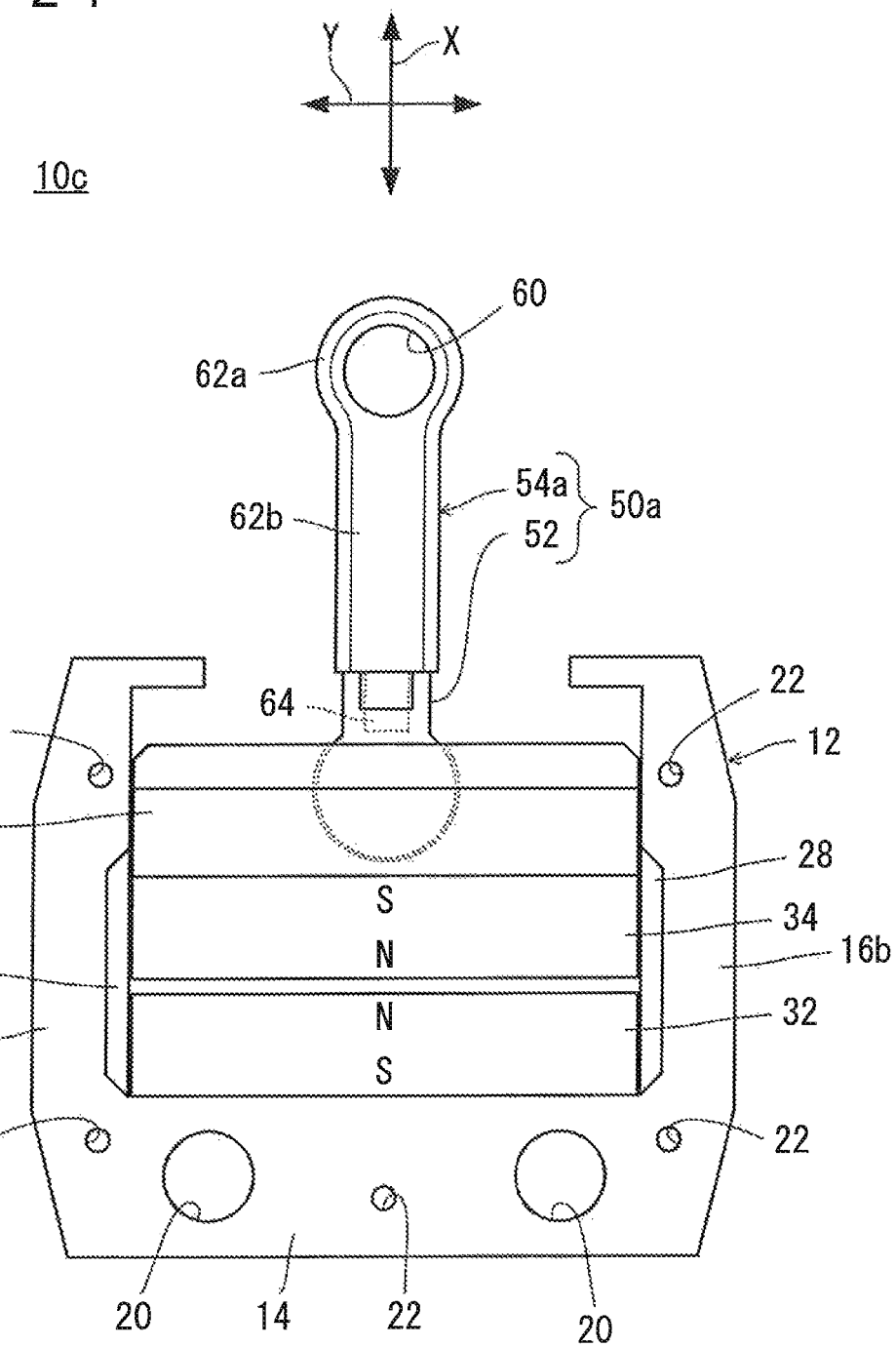
FIG. 21 is a front view showing an external fixation device according to still another embodiment of the present invention.

Like an external fixation device 10c shown in FIG. 21, a ball joint 50a which is longer than the ball joint 50 by, e.g., 30 mm, may be utilized to fit for patients of specific body sizes. The ball joint 50a has its second shaft portion 54a has a tube-like portion 62a which has the through-hole 60; a leg portion 62b which extends from the tube-like portion 62a; and the male-threaded portion 64. Other arrangements are the same as in the external fixation device 10, so description therefor will not be repeated.

According to the external fixation device 10c as described, it is possible to treat tall patients, for example, even if a large gap must be provided between a position to attach the first pins P1 and a position to attach the second pin P2 in the knee joint A.

Figure 22:
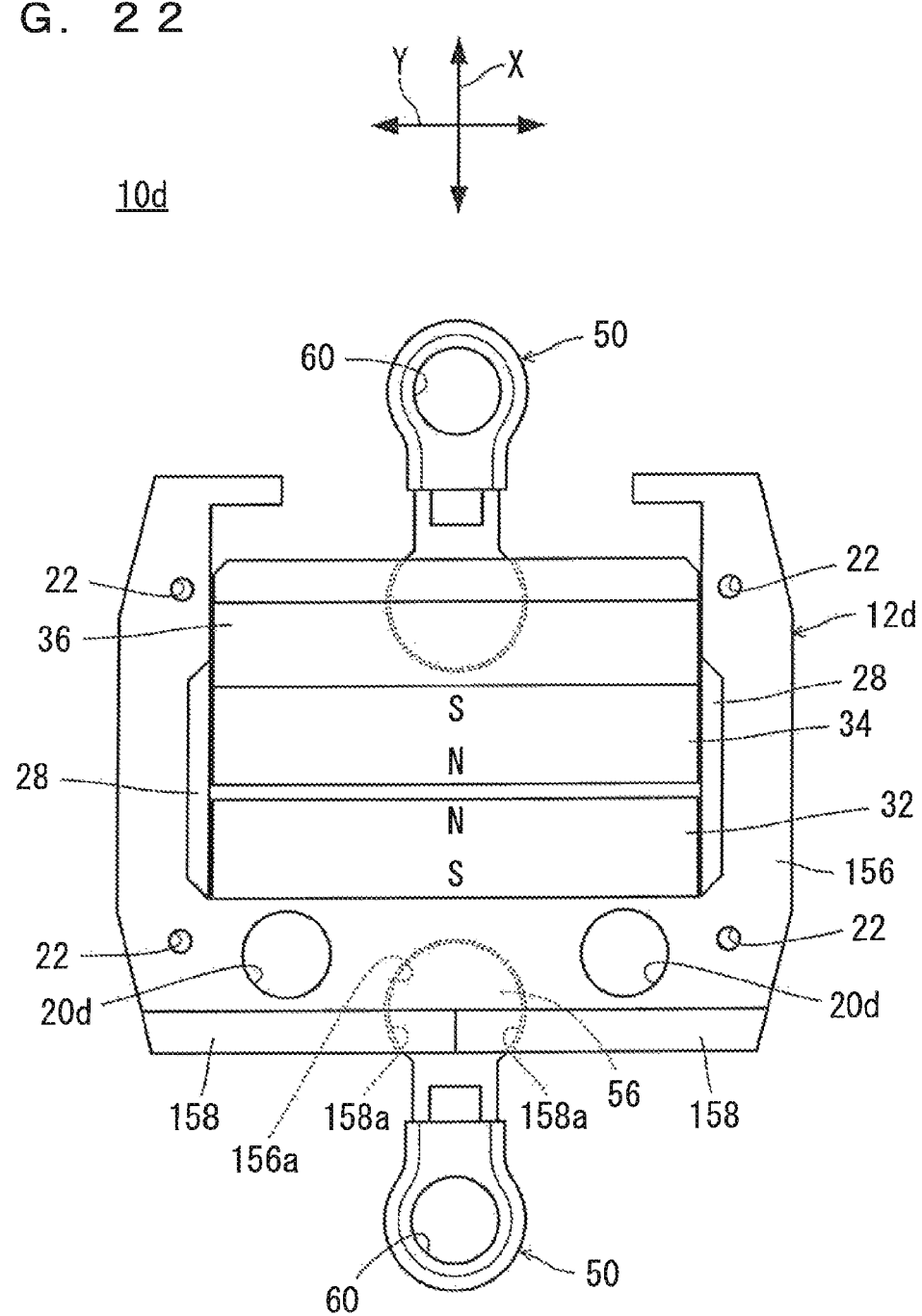
FIG. 22 is a front view showing an external fixation device according to still another embodiment of the present invention.

Like an external fixation device 10d shown in FIG. 22, there may be an arrangement where a frame portion 12d is not only formed with two through-holes 20d but also have a ball joint 50 attached thereto. In this case, the frame portion 12d includes a substantially U-shaped frame main body 156, and two support members 158 as split halves. The frame main body 156 has a hemispherical recess 156a, whereas the support member 158 has a semicircular recess 158a. The ball portion 56 of the ball joint 50 is inserted into the recess 156a in the frame main body 156, and then the frame main body 156 and the two support members 158 are assembled together to surround an exposed region of the ball portion 56 with the two recesses 158a. Under this state, the frame main body 156 and the two support members 158 are integrally assembled with unillustrated fasteners. Two surfaces of the frame portion 12d which are perpendicular to the third direction are formed with eight (four in each surface) screw holes 22. Other arrangements are the same as in the external fixation device 10, so description therefor will not be repeated.

According to the external fixation device 10d as described, since the frame portion 12d is provided with the through-holes 20d and the ball joint 50, the first pins P1 may be inserted through whichever of the through-holes 20d and/or the through-hole 60 of the ball joint 50 depending on situations. This increases convenience.

Figure 23:
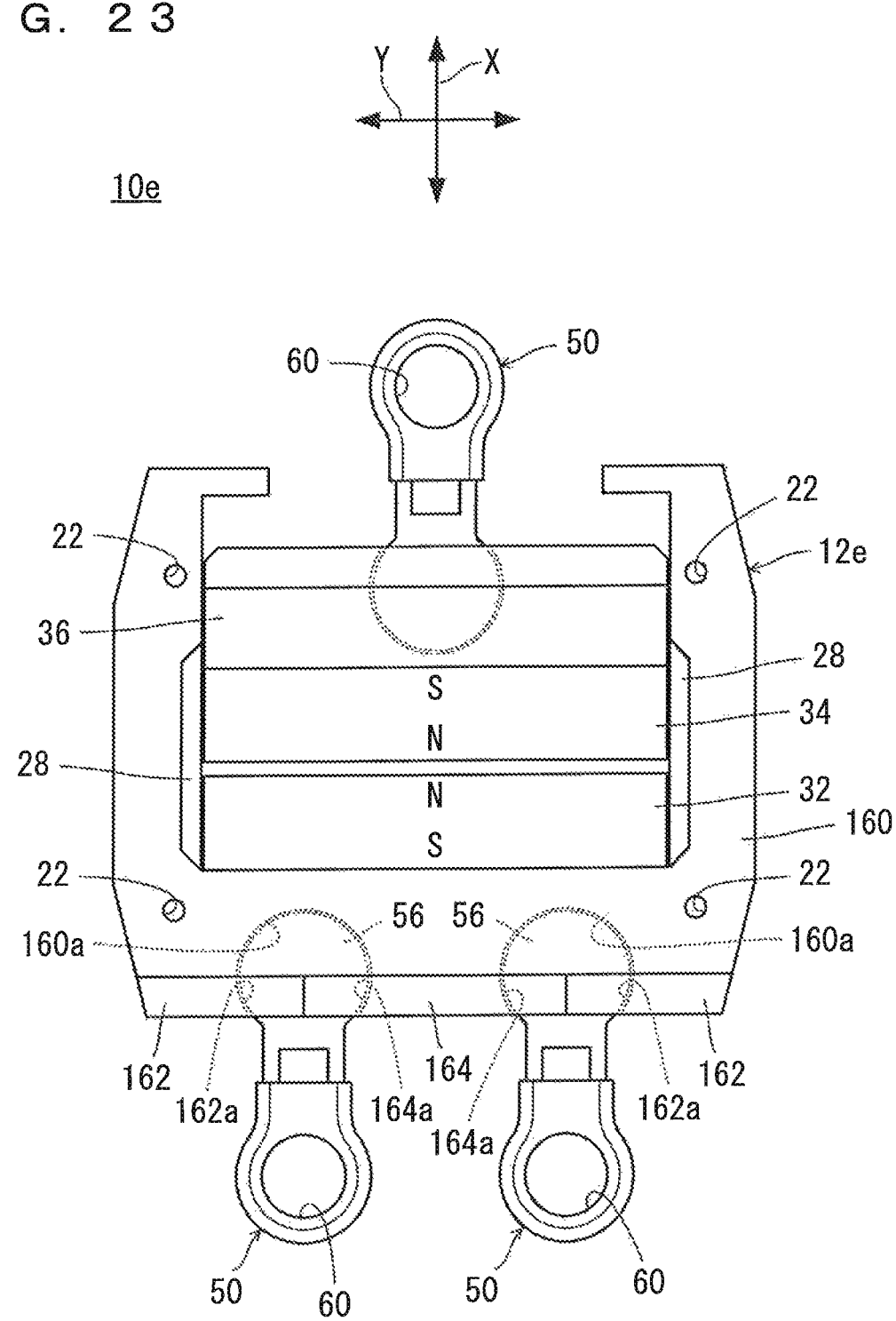
FIG. 23 is a front view showing an external fixation device according to still another embodiment of the present invention.

Like an external fixation device 10e shown in FIG. 23, there may be an arrangement that not only the ball joint 50 is attached to the second holding portion 36 but also two ball joints 50 are attached to a frame portion 12e. In this case, the frame portion 12e includes a substantially U-shaped frame main body 160; two support members 162 on two ends; and a support member 164 in a center. The frame main body 160 has two hemispherical recesses 160a; the support member 162 has a semicircular recess 162a; and the support member 164 has two end regions each formed with a semicircular recess 164a. The two ball portions 56 of the ball joints 50 are inserted into the two recesses 160a in the frame main body 160, and then the frame main body 160, the support member 164 and the two support members 162 are assembled together to surround exposed regions of the ball portions 56 with the recesses 162a and the recess 164a. Under this state, the frame main body 160, the support member 164 and the two support members 162 are integrally assembled with unillustrated fasteners. Two surfaces of the frame main body 160 which are perpendicular to the third direction are formed with eight (four in each surface) screw holes 22. Other arrangements are the same as in the external fixation device 10, so description therefor will not be repeated.

According to the external fixation device 10e as described, freedom of movement of the knee joint A is further improved.

Figure 24:
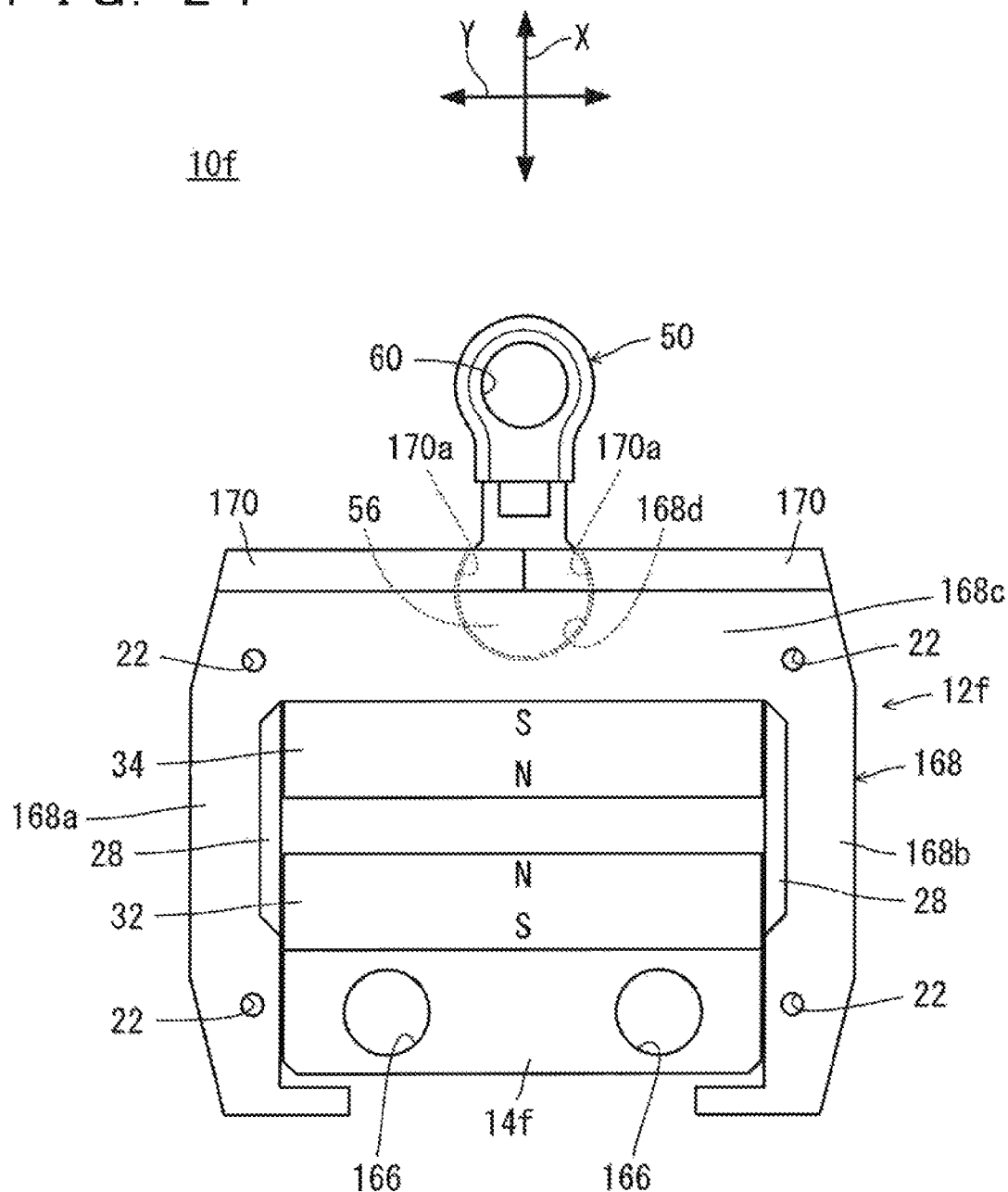
FIG. 24 is a front view showing an external fixation device according to still another embodiment of the present invention.

Like an external fixation device 10f shown in FIG. 24, the ball joint 50 may be attached to a frame portion 12f, and a first holding portion 14f may be formed with two through-holes 166. In this case, the frame portion 12f includes a substantially U-shaped frame main body 168, and two support members 170 as split halves. The frame main body 168 includes first limiter portions 168a, 168b, and a connecting portion 168c which connects the first limiter portions 168a, 168b to each other. The connecting portion 168c of the frame main body 168 has a hemispherical recess 168d, whereas the support members 170 have semicircular recesses 170a. The ball portion 56 of the ball joint 50 is inserted into the recess 168d in the connecting portion 168c, and then the frame main body 168 and the two support members 170 are assembled together to surround an exposed region of the ball portion 56 with the two recesses 170a. Under this state, the frame main body 168 and the two support members 170 are integrally assembled with unillustrated fasteners. The first permanent magnet 32 is disposed on an inner surface of the first holding portion 14f, whereas the second permanent magnet 34 is disposed on an inner surface of the connecting portion 168c. Two surfaces of the frame portion 12f which are perpendicular to the third direction are formed with eight (four in each surface) screw holes 22. With the above, the first pin P1 is inserted through each of the two through-holes 166 formed in the first holding portion 14f, whereas the second pin P2 is inserted through the through-hole 60 of the ball joint 50 which is attached to the frame portion 12f. In this embodiment, the connecting portion 168c and the two support members 170 represent the second holding portion. Therefore, in the external fixation device 10f, the first limiter portions 168a, 168b and the second holding portion are formed integrally with each other.

The external fixation device 10f as described provides substantially the same advantages as offered by the external fixation device 10.

Figure 25:
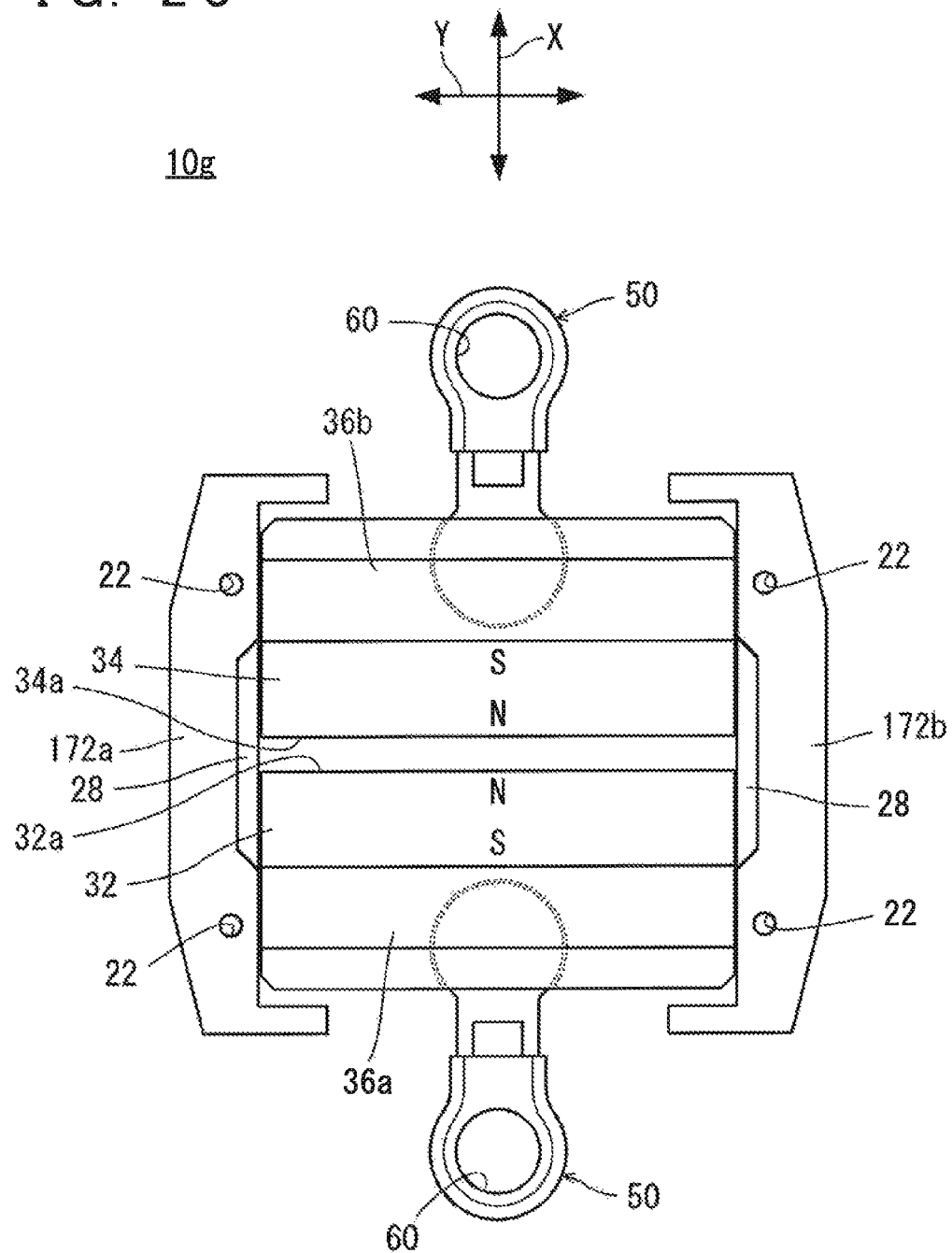
FIG. 25 is a front view showing an external fixation device according to still another embodiment of the present invention.
Figure 26:
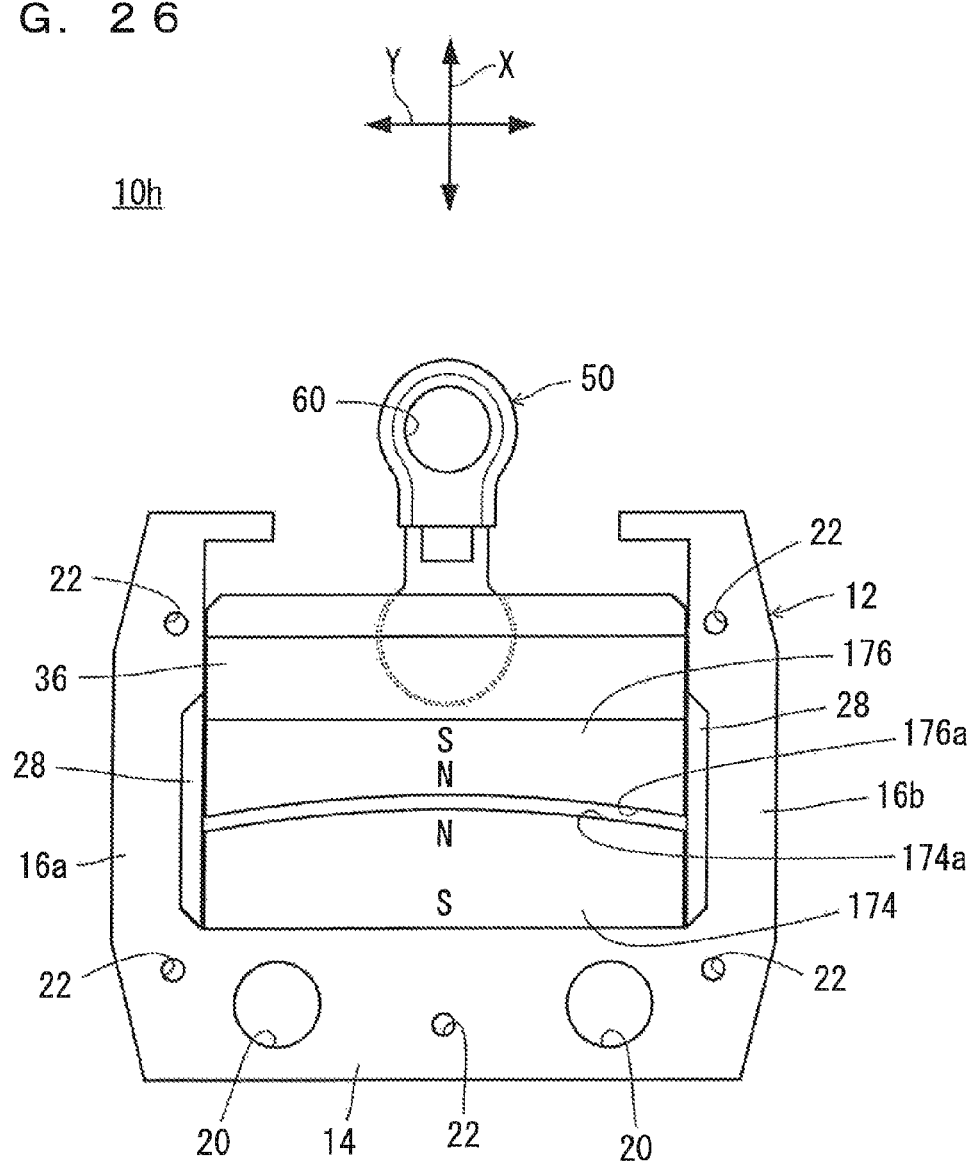
FIG. 26 is a front view showing an external fixation device according to still another embodiment of the present invention.

Like an external fixation device 10g shown in FIG. 25, there may be an arrangement that two first limiter portions 172a and 172b are not connected to each other by the first holding portion 36a or the second holding portion 36b. The first holding portion 36a and the second holding portion 36b have the same configuration as the second holding portion 36 which is included in the external fixation device 10. The external fixation device 10g includes a first permanent magnet 32 and a second permanent magnet 34 which are disposed with their same poles opposed to each other. The first holding portion 36a is attached to a surface of the first permanent magnet 32 which faces away from the opposing surface 32a, whereas the second holding portion 36b is attached to a surface of the second permanent magnet 34 which faces away from the opposing surface 34a. Each of the first holding portion 36a and the second holding portion 36b is connected to a respective ball joint 50. The first permanent magnet 32, the second permanent magnet 34, the first holding portion 36a and the second holding portion 36b described above are sandwiched from their sides (the second direction) by two plate-like first limiter portions 172a, 172b. Two surfaces of the first limiter portion 172a which are perpendicular to the third direction are formed with four (two in each surface) screw holes 22. Likewise, two surfaces of the first limiter portion 172b which are perpendicular to the third direction are formed with four (two in each surface) screw holes 22. The first pin P1 is inserted through the ball joint 50 on the first permanent magnet 32 side, whereas the second pin P2 is inserted through the ball joint 50 on the second permanent magnet 34 side.

According to the external fixation device 10g as described, freedom of movement of the knee joint A is improved further since each of the first permanent magnet 32 and the second permanent magnet 34 is movable in the first direction.

The shape of the permanent magnets is not limited to a rectangular parallelepiped. Like an external fixation device 10h shown in FIG. 26, a first permanent magnet 174 which has a convexed opposing surface 174a and a second permanent magnet 176 which has a concaved opposing surface 176a may be utilized. Other arrangements are the same as in the external fixation device 10, so description therefor will not be repeated.

According to the external fixation device 10h as described, it is possible to increase the area of opposing surfaces of the first permanent magnet 174 and the second permanent magnet 176, which makes it possible to further increase the repulsion force.

Figure 27:
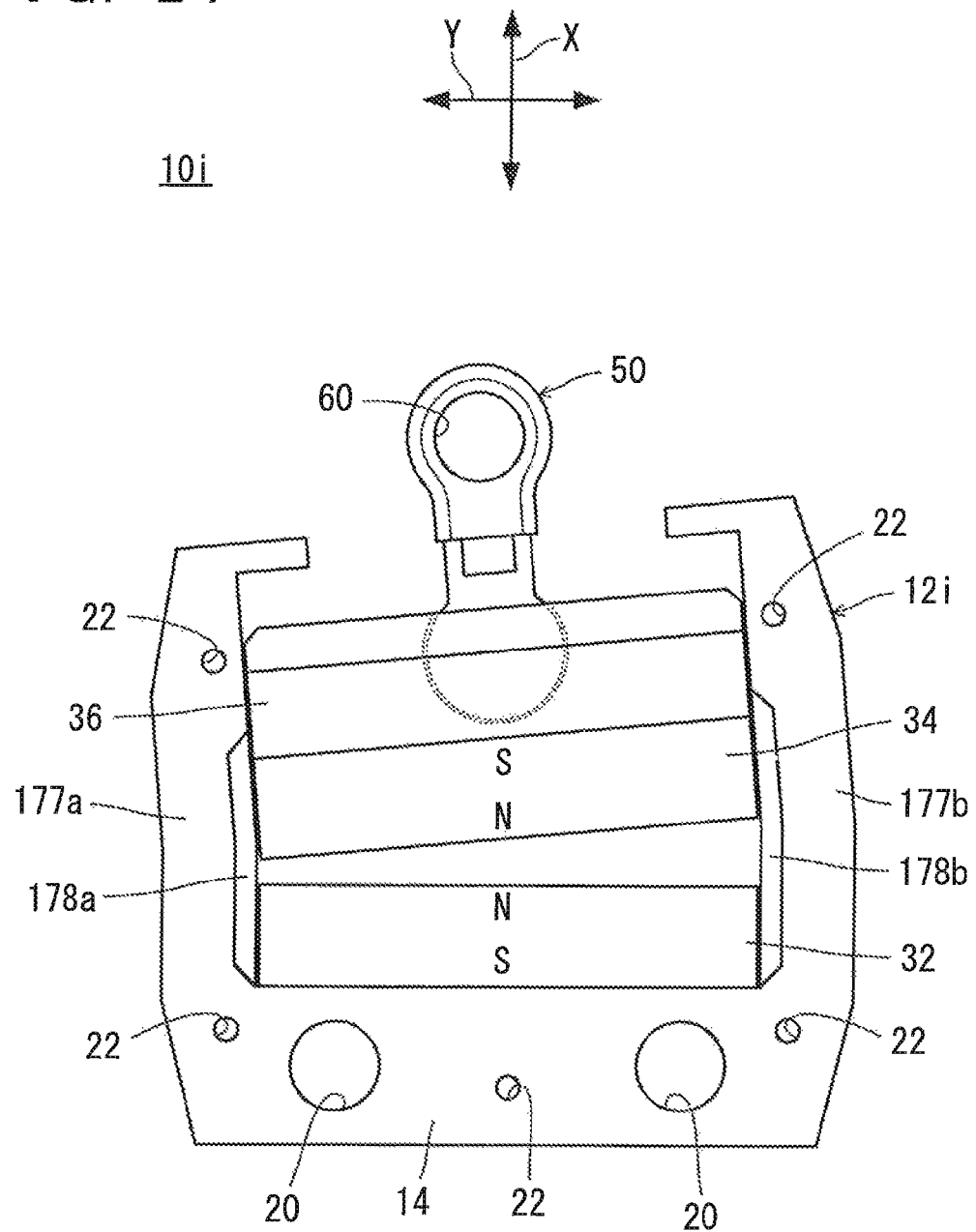
FIG. 27 is a front view showing an external fixation device according to still another embodiment of the present invention.

Like an external fixation device 10i shown in FIG. 27, both of first limiter portions 177a and 177b of the frame portion 12i may be slanted in one direction. Accordingly, nonmagnetic platy members 178a, 178b disposed on an inner side surface of the frame 12i are also slanted. Other arrangements are the same as in the external fixation device 10, so description therefor will not be repeated.

According to the external fixation device 10i as described, it is possible to move the second permanent magnet 34 in a direction slanted from the first direction (oblique direction) with respect to the first permanent magnet 32.

Figure 28:
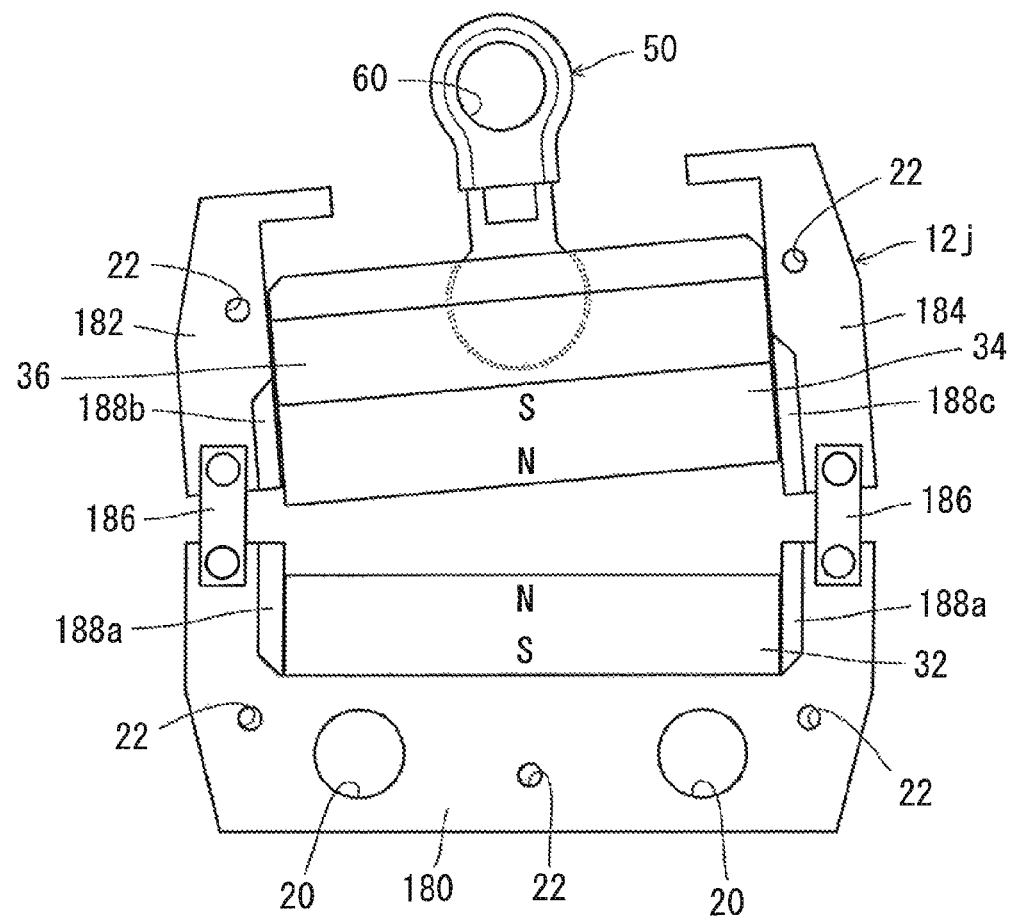
FIG. 28 is a front view showing an external fixation device according to still another embodiment of the present invention.

Like an external fixation device 10j shown in FIG. 28, part of a frame portion 12j may be movable in a left-right direction. The frame portion 12j is structured like the frame portion 12 in FIG. 2 but in three pieces, i.e., a first frame 180, a second frame 182 and a third frame 184. The first frame 180 and the second frame 182 are connected to each other by a connecting member 186, whereas the first frame 180 and the third frame 184 are connected to each other by a connecting member 186. Also, the first frame 180 has its inner side surfaces formed with two platy members 188a; the second frame 182 has its inner side surface formed with a platy member 188b; and the third frame 184 has its inner side surface formed with a platy member 188c. The platy members 188a, 188b and 188c are nonmagnetic, preferably being formed of a nonmagnetic stainless steel such as SUS304, aluminum, titanium, etc. In the external fixation device 10j, second limiter portions are attached individually, i.e., for the first frame 180, for the second frame 182 and the third frame 184. Other arrangements are the same as in the external fixation device 10, so description therefor will not be repeated.

According to the external fixation device 10j as described, it is possible to move the second permanent magnet 34 in the second direction (left-right direction).

Figure 29:
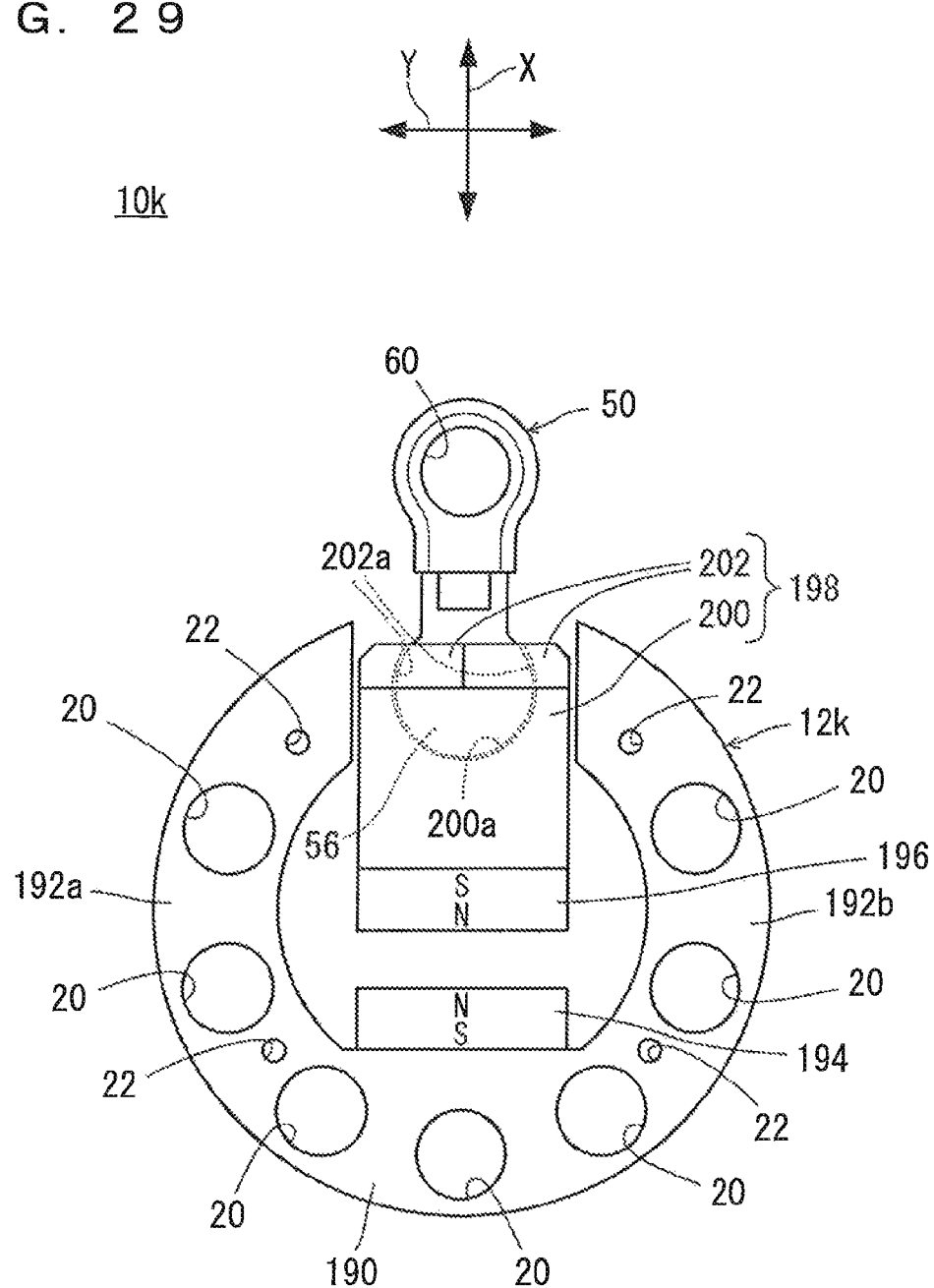
FIG. 29 is a front view showing an external fixation device according to still another embodiment of the present invention.

Like an external fixation device 10k shown in FIG. 29, a substantially C-shaped frame portion 12k may be utilized. The frame portion 12k includes a first holding portion 190, and a pair of first limiter portions 192a, 192b extending like arcs from two ends of the first holding portion 190. The frame portion 12k is formed with a plurality (seven, in the present embodiment) of through-holes 20, and a plurality (eight, in the present embodiment (four in each surface which is perpendicular to the third direction)) of screw holes 22. The first holding portion 190 has its inner surface, to which a rectangular parallelepiped first permanent magnet 194 is attached, whereas a second permanent magnet 196 is disposed to oppose the first permanent magnet 194. The first permanent magnet 194 and the second permanent magnet 196 are disposed with their same poles opposed to each other. The second permanent magnet 196 is held by a second holding portion 198 which is movable in a gap between two end portions of the frame portion 12k. The second holding portion 198 includes a first support member 200 attached to the second permanent magnet 196, and two second support members 202 as halves. The first support member 200 has a hemispherical recess 200a, whereas each of the second support members 202 has a semicircular recess 202a. The ball portion 56 of the ball joint 50 is inserted into a recess 200a in the first support member 200, and then the first support member 200 and the two second support members 202 are assembled together to surround an exposed region of the ball portion 56 with the two recesses 202a. Under this state, the first support member 200 and the two second support members 202 are integrally assembled with unillustrated fasteners. As described above, the ball joint 50 is connected to the second holding portion 198.

According to the external fixation device 10k as described, it is possible to obtain a substantially cylindrical device, and it is possible to dispose a plurality of through-holes 20 in an annular pattern in the frame portion 12k. Therefore, it becomes possible to adjust a distance between the first pins P1 and the second pin P2 by selecting the through-holes 20 to insert the first pins P1.

Figure 30:
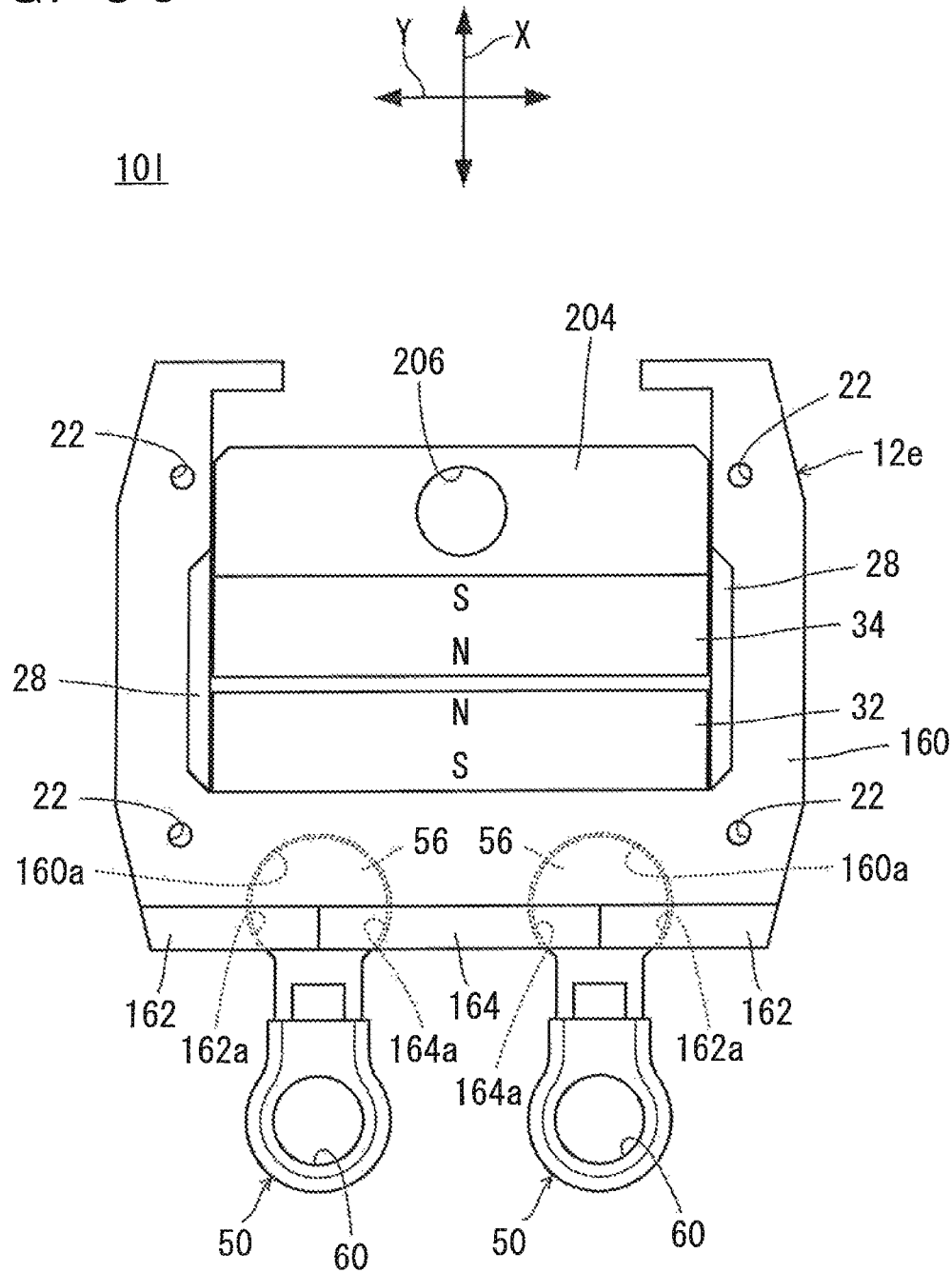
FIG. 30 is a front view showing an external fixation device according to still another embodiment of the present invention.

Like an external fixation device 10l shown in FIG. 30, a through-hole 206 may be formed in a second holding portion 204 which holds the second permanent magnet 34. In this case, the ball joint 50 is not attached to the second holding portion 204, and the second pin P2 is inserted through the through-hole 206. Other arrangements are the same as in the external fixation device 10e shown in FIG. 23, so description therefor will not be repeated.

According to the external fixation device 10l as described, substantially the same advantages provided by the external fixation device 10 are obtained even if the ball joint 50 is not attached on the second pin P2 side, since the ball joint 50 is attached to the first pin P1 side.

Figure 31:
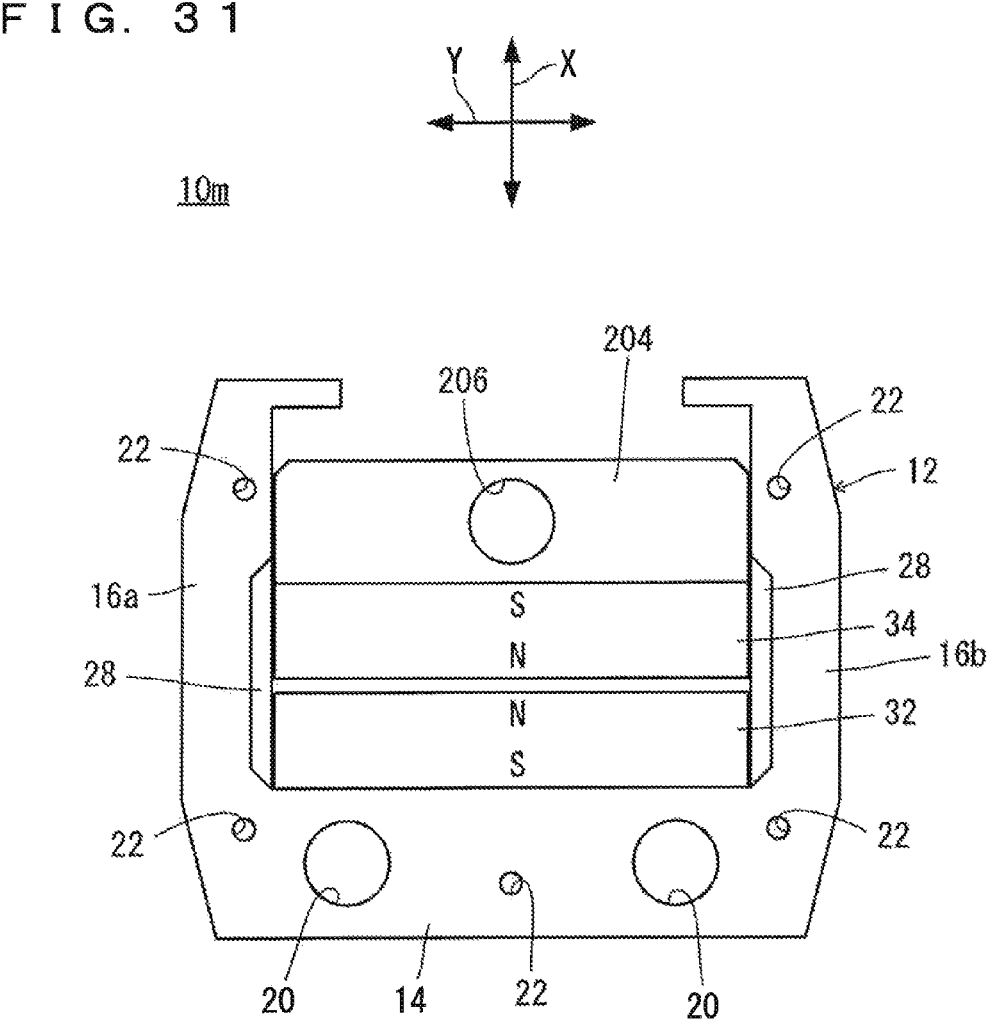
FIG. 31 is a front view showing an external fixation device according to still another embodiment of the present invention.

Like an external fixation device 10m shown in FIG. 31, it is acceptable even if the ball joint 50 is not included. In the external fixation device 10m, the first permanent magnet 32 is held by the frame portion 12 shown in FIG. 2; the second permanent magnet 34 is held by a second holding portion 204 shown in FIG. 30; the first pins P1 are inserted through the through-holes 20; and the second pin P2 is inserted through a through-hole 206.

As exemplified in the external fixation device 10m, the present invention need not necessarily include the ball joint 50.

In the present invention, the number of ball joints attached to the first holding portion, and the number of through-holes formed in the first holding portion may be one or plural.

Figure 32:
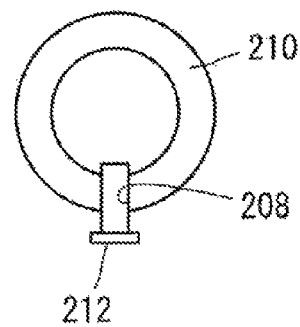
FIG. 32 is an illustrative drawing showing another example of the stopper.
Figure 33:
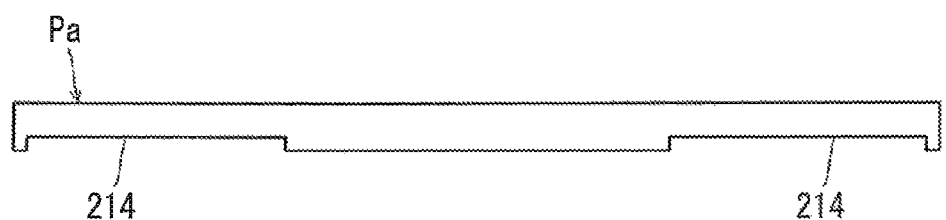
FIG. 33 is an illustrative drawing showing another example of the pin.

In the embodiment described above, as shown in FIG. 15 and in FIG. 19, the nuts 146 are used as stoppers when attaching the external fixation device and the pin fixture 100 to the first pins P1 and the second pin P2. However, the stoppers are not limited to this. As shown in FIG. 32 for example, a stopper may be provided by a ring member 210 which has a screw hole 208 penetrating in a radial direction and a bolt 212 threaded through the screw hole 208. In this case, at least one of the first pin and the second pin is provided by a pin Pa as shown in FIG. 33. The pin Pa is rod-like, and has flat surfaces 214 on its two end portions. The flat surfaces 214 are wider than the place where the external fixation device, the pin fixture 100 and the ring member 210 are attached. Thus, the ring member 210 is movable axially of the pin Pa even if the bolt 212 threaded through the ring member 210 is in contact with the flat surface 214.

Since the ring member 210 attached to the pin Pa is movable axially of the pin Pa as described, the external fixation device and the pin fixture 10 which are attached to the pin Pa are movable axially of the pin Pa, making it possible to move the knee joint A more freely.

Figure 34:
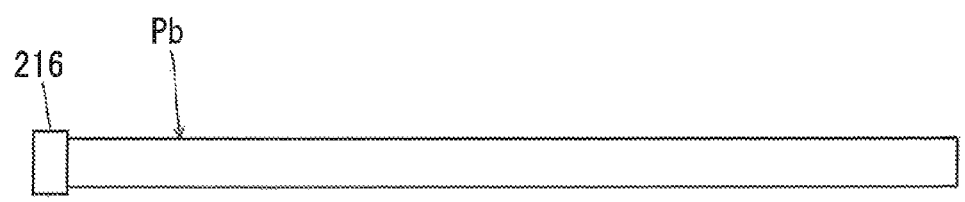
FIG. 34 is an illustrative drawing showing another example of the pin.

As shown in FIG. 34, the first pins and the second pin may be provided by a pin Pb which has a head portion 216.

In regard to the external fixation device 10, there may be arrangements as shown in FIG. 3, in alternate long and short dash lines, that the frame portion 12 is formed with the screw holes 218 which provides communication between an outer surface of the frame portion 12 and the through-holes 20; and as shown in FIG. 8, in alternate long and short dash lines, the second shaft portion 54 of the ball joint 50 is formed with a screw hole 220 which provides communication between an outer surface of the tube-like portion 62 and the through-hole 60. Further, in regard to the pin fixture 100, there may be arrangements that as shown in FIG. 12, in alternate long and short dash lines, the fixture main body 102 is formed with a screw hole 222 which provides communication between an outer surface of the thick portion 108 and the through-hole 118; as shown in FIG. 13, in alternate long and short dash lines, the first connecting portion 104 is formed with a screw hole 224 which provides communication between an outer surface of the thick portion 124 and the through-hole 128; and as shown in FIG. 14, in alternate long and short dash lines, the second connecting portion 106 is formed with a screw hole 226 which provides communication between an outer surface of the thick portion 132 and the through-hole 136.

In these cases, it is possible to fix the first pins P1 and the second pin P2 by threading the bolt 212 shown in FIG. 32 into the screw holes 218, 220, 222, 224 and 226, without using the nuts 146 or the ring members 210.

Further, the first pins P1 and the second pin P2 may have their end portions provided with resin caps to prevent the external fixation device and the pin fixture 100 from coming off the first pins P1 and the second pin P2.

The first permanent magnet 32b and the second permanent magnet 34b as shown in FIG. 20 may also be used in the external fixation device shown in FIG. 21 through FIG. 31. Also, the first permanent magnet and the second permanent magnet may be disposed to have their S poles to oppose to each other, with their respective N poles on the outer side.

Figure 35:
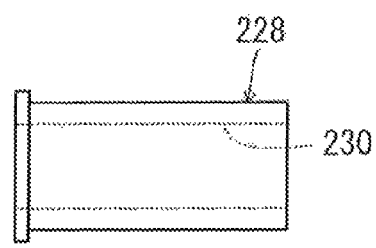
FIG. 35 is a side view showing another example of the sleeve.

In the external fixation device 10a shown in FIG. 17, the slanted sleeve 148 may be replaced with an ordinary sleeve 228 as shown in FIG. 35. The sleeve 228 has a through-hole 230, which is not slanted with respect to an axis direction of the sleeve 228. The sleeve 228 is nonmagnetic, preferably being formed of a nonmagnetic stainless steel such as SUS304, aluminum, titanium, etc. Also, the slanted sleeve 148 may be replaced with a hollow tube-like member which has flexibility like resin or rubber.

A plurality of slanted sleeves may be used in one external fixation device. Also, the slanted sleeve may be fitted into a through-hole formed in the second holding portion.

The first holding portion and the pair of first limiter portions in the frame portion may be assembled together with fasteners such as bolts.

The present invention is applicable not only to knee joints but also any other joints such as ankle joints, hip joints, hand joint, elbow joints and finger joints. In these cases, locations and numbers of through-holes and ball joints may be modified depending on the body part.

The present invention being thus far described in terms of preferred embodiments, it is obvious that these may be varied in many ways within the scope and the spirit of the present invention. The scope of the present invention is only limited by the accompanied claims.

REFERENCE SIGNS LIST

10, 10a through 10m External fixation devices
12, 12a, 12d, 12e, 12f, 12i, 12j, 12k Frame portions
14, 14f, 36a, 190 First holding portions
16a, 16b, 168a, 168b, 172a, 172b, 177a, 177b, 192a, 192b First limiter portions
20, 20a, 20d, 60, 74, 74a, 80, 80a, 118, 128, 130, 136, 138, 154, 166, 206, 230 Through-holes
32, 32b, 174, 194 First permanent magnets
32a, 34a, 174a, 176a Opposing surfaces
34, 34b, 176, 196 Second permanent magnets
36, 36b, 198, 204 Second holding portions
50, 50a Ball joints
66, 66a Second limiter portions
100 Pin fixture
102 Fixture main body
104 First connecting portion
106 Second connecting portion
140, 144, 212 Bolts
146 Nut
148 Slanted sleeve
210 Ring member
A Knee joint
B First bone portion
C Second bone portion
P1 First pin
P2 Second pin
Pa, Pb Pins
S Fixation device set
X First direction
Y Second direction
Z Third direction

The invention claimed is:

1. An external fixation device for keeping a first bone portion and a second bone portion separated from each other in a joint, by attaching to a first pin which penetrates the first bone portion and to a second pin which penetrates the second bone portion, the device comprising:
  a first permanent magnet and a second permanent magnet which are opposed to each other, with their same poles facing each other;
  a first holding portion which is disposed on a surface of the first permanent magnet, on a side facing away from a surface opposing to the second permanent magnet, and is attached to the first pin;
  a second holding portion which is disposed on a surface of the second permanent magnet, on a side facing away from a surface opposing to the first permanent magnet, and is attached to the second pin;
  a pair of first limiter portions which allow movement of the first permanent magnet and the second permanent magnet in a first direction defined as a direction of their repulsion force by sandwiching the first permanent magnet and the second permanent magnet from a second direction defined as a direction perpendicular to the first direction, and limit movement thereof in the second direction;

a second limiter portion disposed to connect the pair of first limiter portions to each other to limit movement of the first permanent magnet and the second permanent magnet in a third direction defined as a direction perpendicular to both of the first direction and the second direction;

a first platy member provided between one of the first limiter portions and the first and second permanent magnets; and a second platy member provided between the other of the second limiter portions and the first and second permanent magnets; wherein the second limiter portion includes a second platy portion, and a first platy portion provided between the second platy portion and the first and second permanent magnets;

each of the first limiter portions and the second platy portion is magnetic; and each of the first platy member, the second platy member and the first platy portion is nonmagnetic.

2. The external fixation device according to claim 1, further comprising a ball joint for attaching at least one of the first holding portion and the second holding portion to a corresponding one of the first pin and the second pin.

3. The external fixation device according to claim 2, wherein the second holding portion is connected to the ball joint, whereas the first holding portion has a through-hole for insertion of the first pin.

4. The external fixation device according to claim 3, further comprising a slanted sleeve fitted into the through-hole.

5. The external fixation device according to claim 1, wherein
at least one of the first holding portion and the second holding portion has a through-hole for insertion of the corresponding one of the first pin and the second pin.

6. The external fixation device according to claim 1, wherein the pair of first limiter portions and the first holding portion are integral with each other.

7. The external fixation device according to claim 1, wherein each of the first permanent magnet and the second permanent magnet is rectangular parallelepiped.

8. A fixation device set comprising: the external fixation device according to claim 1, for attaching to the first pin and the second pin on their common one end-side; and
a pin fixture for attaching to the first pin and the second pin on their common another end-side; wherein
the pin fixture includes: a fixture main body; a first connecting portion for connecting the fixture main body to the first pin; and a second connecting portion for connecting the fixture main body to the second pin.

9. The fixation device set according to claim 8, wherein the first connecting portion is pivotable with respect to the fixture main body, whereas the second connecting portion is linearly movable with respect to the fixture main body.

* * * * *